United States Patent
Hawkett et al.

(10) Patent No.: US 8,765,183 B2
(45) Date of Patent: Jul. 1, 2014

(54) POLYMER MICROGEL BEADS

(75) Inventors: Brian Stanley Hawkett, Mona Vale (AU); Nirmesh Jain, Paramatta (AU)

(73) Assignee: The University of Sydney (AU)

( * ) Notice: Subject to any disclaimer, the term of this patent is extended or adjusted under 35 U.S.C. 154(b) by 700 days.

(21) Appl. No.: 12/993,047

(22) PCT Filed: May 15, 2009

(86) PCT No.: PCT/AU2009/000619
§ 371 (c)(1),
(2), (4) Date: Apr. 22, 2011

(87) PCT Pub. No.: WO2009/137889
PCT Pub. Date: Nov. 19, 2009

(65) Prior Publication Data
US 2011/0190566 A1    Aug. 4, 2011

(30) Foreign Application Priority Data

May 16, 2008    (AU) ................ 2008902428

(51) Int. Cl.
*A61K 9/14*    (2006.01)
(52) U.S. Cl.
USPC ..................................................... 424/489
(58) Field of Classification Search
None
See application file for complete search history.

(56) References Cited

U.S. PATENT DOCUMENTS

| | | |
|---|---|---|
| 2004/0115433 A1 | 6/2004 | Elaissari et al. |
| 2005/0175702 A1 | 8/2005 | Muller-Schulte |
| 2007/0154397 A1 | 7/2007 | Chang et al. |

FOREIGN PATENT DOCUMENTS

| | | |
|---|---|---|
| DE | 198 00 294 | 7/1999 |
| JP | 2005-537342 | 12/2005 |
| JP | 2006-328309 | 12/2006 |
| JP | 2008-516017 | 5/2008 |
| WO | WO 2004/081072 | 9/2004 |
| WO | WO 2006/037161 | 4/2006 |
| WO | WO 2007/097593 | 8/2007 |
| WO | WO 2007/112503 | 10/2007 |

OTHER PUBLICATIONS (http://www.magneticmicrosphere.com/hafeli_lab/other/Bulte_chapter_2001.pdf, accessed Sep. 20, 2013.*
International Search Report of PCT/AU2009/000618, mailed Jul. 13, 2009, 4 pgs.
International Preliminary Report on Patentability of PCT/AU2009/000618, mailed Nov. 17, 2010, 3 pgs.
Arshady, "Microspheres for biomedical applications: preparation of reactive and labelled microspheres", Biomaterials, 1993, vol. 14, No. 1, pp. 5-15.

(Continued)

*Primary Examiner* — Paul Dickinson
(74) *Attorney, Agent, or Firm* — Merchant & Gould P.C.

(57) ABSTRACT

The present invention relates to polymer microgel beads having a polymeric matrix with nanomagnetic particles dispersed substantially uniformly therethrough, wherein a steric stabiliser is associated with the particles, the steric stabiliser being a polymeric material that (i) does not form part of the polymeric matrix of the beads, and (ii) comprises a steric stabilising polymeric segment and an anchoring polymeric segment, wherein the steric stabilising polymeric segment is different from the anchoring polymeric segment, and wherein the anchoring polymeric segment has an affinity toward the surface of the nanomagnetic particles and secures the stabiliser to the particles.

21 Claims, 1 Drawing Sheet

(56) References Cited

OTHER PUBLICATIONS

Cui et al., "Developing a Hybrid Emulsion Polymerization System to Synthesize $Fe_3O_4$/Polystyrene Latexes with Narrow Size Distribution and High Magnetite Content", Journal of Polymer Science: Part A: Polymer Chemistry, Wiley InterScience, 2007, pp. 5285-5295.

Fonnum et al., "Characterisation of Dynabeads® bymagnetization measurements and Mössbauer spectroscopy", Journal of Magnetism and Magnetic Materials, 2005, vol. 293, pp. 41-47.

Gu et al., "Preparation and colloidal stability of monodisperse magnetic polymer particles", Journal of Colloid and Interface Science, 2005, vol. 289, pp. 419-426.

Kim et al., "Magnetomicelles: Composite Nanostructures from Magnetic Nanoparticles and Cross-Linked Amphiphilic Block Copolymers", Nanoletters, 2005, vol. 5, No. 10, pp. 1987-1991.

Liu et al., "Preparation of Magnetic Microspheres from Water-in-Oil Emulsion Stabilized by Block Copolymer Dispersant", Biomacromolecules, 2005, vol. 6, pp. 1280-1288.

Mackova et al., "Magnetic Poly(N-isopropylacrylamide) Microspheres by Dispersion and Inverse Emulsion Polymerization", Journal of Polymer Science: Part A: Polymer Chemistry, Wiley InterScience, 2007, vol. 45, pp. 5884-5898.

Pich et al., "Temperature Sensitive Hybrid Microgels with Magnetic Properties", Langmuir, 2004, vol. 20, No. 24, pp. 10706-10711.

Sauzedde et al., "Hydrophilic magnetic polymer latexes. 1. Adsorption of magnetic iron oxide nanoparticles onto various cationic latexes", Colloid Polym Sci, 1999, vol. 277, pp. 846-855.

Sauzedde et al., "Hydrophilic magnetic polymer latexes. 2. Encapsulation of adsorbed iron oxide nanoparticles", Colloid Polym Sci, 1999, vol. 277, pp. 1041-1050.

Shiho et al., "Magnetic compounds as coatings on polymer particles and magnetic properties of the composite particles", Journal of Materials Chemistry, 2000, vol. 10, pp. 333-336.

Wormuth, "Superparamagnetic Latex via Inverse Emulsion Polymerization", Journal of Colloid and Interface Science, 2001, vol. 241, pp. 366-377.

Zhang et al., "Encapsulation of Magnetic Particles Via Miniemulsion Polymerization of Styrene. II. Effect of Some Parameters on the Polymerization of Styrene", Journal of Applied Polymer Science, Wiley InterScience, 2007, vol. 105, pp. 3525-3530.

\* cited by examiner

POLYMER MICROGEL BEADS

This application is a National Stage Application of PCT/AU2009/000619, filed 15 May 2009, which claims benefit of Ser. No. 2008902428, filed 16 May 2008 in Australia and which applications are incorporated herein by reference. To the extent appropriate, a claim of priority is made to each of the above disclosed applications.

FIELD OF THE INVENTION

The present invention relates in general to polymer microgel beads. In particular, the invention relates to polymer microgel beads incorporating nanomagnetic particles, and to a method of preparing the same. The polymer microgel beads in accordance with the invention are particularly suited for use in biomedical applications such as inducing hyperthermia in tissue, and it will therefore be convenient to describe the invention with an emphasis toward these applications. However, it is to be understood that the polymer microgel beads may be used in various other applications.

BACKGROUND OF THE INVENTION

Polymer beads incorporating magnetic particles are known. Such beads have been found to be particularly suitable for use in biomedical applications. In particular, the beads may be used for therapeutic or analytical purposes. For example, magnetic polymer beads may function as a carrier and permit the guiding and release of a drug at a specific site of a subject. The beads may also be used to provide hyperthermic treatment of tissue such as diseased tissue in a subject. Such polymer beads have also found application in immunoassays.

Numerous techniques have been developed over the years to produce polymer beads incorporating magnetic particles. These include layer-by-layer deposition techniques, classical heterogeneous polymerisation processes (e.g. emulsion, suspension, dispersion, microemulsion, and miniemulsion techniques), and the precipitation of magnetic materials within the pores of preformed polymer beads.

For most biomedical applications, it is generally important that the beads be produced with a uniform size and composition and with a relatively high magnetic particle content. Furthermore, it is also generally important that the magnetic particles be substantially uniformly dispersed throughout the polymer bead.

A considerable amount of research has been conducted to date on dispersion techniques for preparing polymer beads incorporating magnetic particles. Such techniques include the aforementioned classical heterogeneous polymerisation processes, which typically involve dispersing magnetic particles in a liquid phase and polymerising monomer to form polymer that encapsulates the particles.

Despite some success, the complexity of polymer particle nucleation in conventional dispersion polymerisation processes and the difficulties associated with controlling the stability of the dispersed magnetic particles have proven to be major obstacles in preparing the polymer beads efficiently and with high magnetic particle content. For example, the principle locus for particle nucleation in conventional emulsion polymerisation processes is generally either in the aqueous phase or in monomer-swollen micelles. However, the presence of magnetic particles dispersed in the aqueous phase can provide for additional nucleation sites at the surface of these particles. Accordingly, competition between these mechanisms can result in the formation of polymer beads with little or no magnetic particle content.

The effectiveness of dispersion techniques can also become problematic as the polymer beads are prepared with progressively small magnetic particles. In particular, as the magnetic particles become smaller (for example ≤100 nm) it becomes increasingly more difficult to maintain the particles in a dispersed state so as to produce beads having the particles substantially uniformly distributed therein (i.e. it becomes difficult to prevent aggregation of the magnetic particles during bead manufacture).

An opportunity therefore remains to address or ameliorate one or more disadvantages or shortcomings associated with existing polymer beads incorporating magnetic particles and/or their methods of manufacture, or to at least provide a useful alternative to conventional polymer beads incorporating magnetic particles and/or their methods of manufacture.

SUMMARY OF THE INVENTION

The present invention therefore provides a method of preparing polymer microgel beads incorporating nanomagnetic particles, the method comprising:
providing a dispersion comprising a continuous organic phase and a dispersed aqueous phase, the dispersed aqueous phase comprising:
(i) one or more ethylenically unsaturated monomers that are soluble in the aqueous phase; and
(ii) nanomagnetic particles dispersed throughout the aqueous phase, the particles being maintained in their dispersed state by a steric stabiliser, wherein the steric stabiliser is a polymeric material comprising a steric stabilising polymeric segment and an anchoring polymeric segment, wherein the steric stabilising polymeric segment is different from the anchoring polymeric segment, and wherein the anchoring polymeric segment has an affinity toward the surface of the particles and secures the stabiliser to the particles; and
polymerising the one or more ethylenically unsaturated monomers to thereby form the polymer microgel beads incorporating the nanomagnetic particles.

It has now been found that a steric stabiliser used in accordance with the invention can provide for a highly stable dispersion of nanomagnetic particles within the aqueous phase/monomer composition. The steric stabiliser is particularly effective at stabilising nanomagnetic particles of a size of less than about 100 nm, for example of less than about 50 nm or less than 20 nm.

The polymer matrix of the microgel beads, which in effect encapsulates the nanomagnetic particles, can advantageously be prepared in a controlled, reproducible and efficient manner. It has therefore been possible to prepare the polymer microgel beads to a desired size with a relatively high (e.g. up to about 70 wt. %, relative to the total mass of the bead) substantially uniformly distributed magnetic particle content.

The present invention therefore also provides polymer microgel beads having a polymeric matrix with nanomagnetic particles dispersed substantially uniformly therethrough, wherein a steric stabiliser is associated with the particles, the steric stabiliser being a polymeric material that (i) does not form part of the polymeric matrix of the beads, and (ii) comprises a steric stabilising polymeric segment and an anchoring polymeric segment, wherein the steric stabilising polymeric segment is different from the anchoring polymeric segment, and wherein the anchoring polymeric segment has an affinity toward the surface of the nanomagnetic particles and secures the stabiliser to the particles.

The polymer microgel beads in accordance with the invention may be used in a variety of biomedical applications. For example, the beads may be used to treat a disease or condition in a subject.

Accordingly, the present invention also provides a composition suitable for administration to a subject, the composition comprising polymer microgel beads in accordance with the invention and a pharmacologically acceptable carrier.

In one embodiment, the composition in accordance with the invention is for hyperthermia therapy.

In a further embodiment, there is provided use of composition in accordance with the invention for hyperthermia therapy.

In another embodiment, there is provided a method of performing hyperthermia therapy on a target site of interest in a subject, the method comprising administering a composition according to the invention to the subject and exposing at least the target site to a magnetic field of clinically acceptable frequency and strength to promote the hyperthermia therapy.

In a further embodiment, there is provided use of a composition in accordance with the invention in the manufacture of a formulation for performing hyperthermia therapy.

In another embodiment, there is provided a method for heating a target site of interest in a subject, the method comprising:
(i) administering a composition in accordance with the invention to the subject; and
(ii) exposing at least the target site to a magnetic field of a clinically acceptable frequency and strength such that microgel beads from the composition radiate heat at the target site.

In some applications it may be desirable to image the polymer microgel beads once they have been administered to a subject. The beads may therefore comprise a radioactive isotope for imaging purposes.

Further aspects of the invention appear below in the detailed description of the invention.

BRIEF DESCRIPTION OF THE DRAWINGS

The invention will also be described herein with reference to the following non-limiting drawings in which.

DETAILED DESCRIPTION OF THE INVENTION

Figure 1:
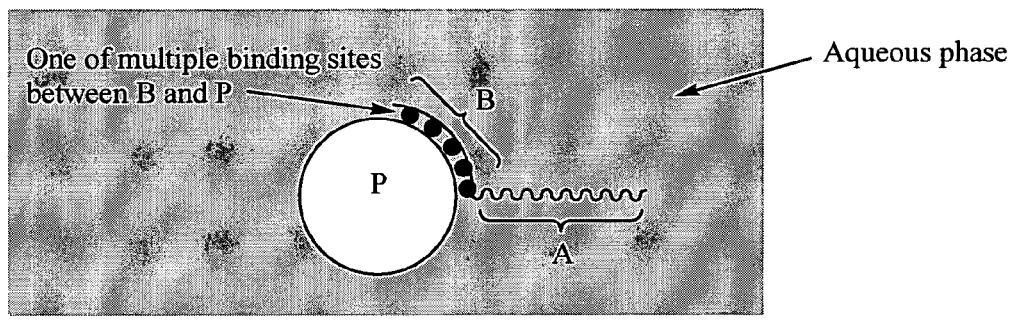
FIG. 1 presents a simplified schematic illustration not to scale showing: the multiple binding interactions between the anchoring polymeric segment (B) and a nanomagnetic particle (P), and the steric stabilising segment (A) solubilised in the aqueous phase. The aqueous phase also comprises monomer (not shown)

As used herein, the expression "polymer microgel" is intended to mean a crosslinked three dimensional network of polymer chains that collectively form a polymer matrix that can absorb and be swollen by an aqueous liquid. By the beads having a polymer matrix that can absorb and be swollen by an aqueous liquid, it will be appreciated that the polymer chains that form the matrix are in effect tethered together such that they can not be fully solvated (i.e. where the bead structure is destroyed) by the aqueous liquid.

the steric stabiliser used in accordance with the invention does not form part of or is independent from the polymeric matrix that forms the polymer microgel beads.

The term "beads" used in conjunction with the expression "polymer microgel" is intended to convey that the polymer microgel mass is in the form of a discrete shape. There is no particular limitation regarding the discrete shape the beads may take, but they will generally be spheroidal.

As will be discussed in more detail below, the size of the polymer microgel beads may be effectively and efficiently tailored during the method of the invention through control of the size and composition of the aqueous phase droplets dispersed throughout the continuous organic phase.

The size of the beads that are to be produced will generally be dictated by their intended application. Generally, the beads will have a size ranging from about 100 nm to about 200 microns, for example from about 10 to about 100 microns, or from about 10 to about 50 microns. In some applications, it may be desirable that the beads have a size ranging from about 20 to about 50 microns. The beads can advantageously be prepared so as to have a size of less than about 10 microns, for example from about 500 nm to about 10 microns, or from about 1 micron to about 10 microns.

For avoidance of any doubt, reference herein to the "size" of the polymer microgel beads or nanomagnetic particles is intended to denote an average size of the beads or particles based on the largest dimension of a given bead or particle. Polymer microgel beads having a size of about 1 micron or more are to be determined by light microscopy, whereas the nanomagnetic particles and polymer microgel beads having a size of less than about 1 micron are to be determined by Transmission Electron Microscopy (TEM).

The polymer microgel beads in accordance with the invention incorporate nanomagnetic particles. By the beads "incorporating" nanomagnetic particles is meant that the particles are retained within and throughout the polymeric matrix of each polymer microgel bead. The method in accordance with the invention advantageously enables the nanomagnetic particles to be distributed substantially evenly or uniformly throughout the polymeric matrix of the beads. Furthermore, the nanomagnetic particles can be distributed in this manner as individual or primary particles (i.e. in a substantially non-aggregated form).

The polymer microgel beads in accordance with the invention can advantageously have a low through to high nanomagnetic particle content. For example, the beads may contain up to about 10 wt %, or up to about 20 wt %, or up to about 30 wt %, or up to about 40 wt %, or up to about 50 wt %, or up to about 60 wt %, or even up to about 70 wt % of nanomagnetic particles, relative to the total mass of the beads. The beads may therefore contain at least 10 wt %, or at least about 20 wt %, or at least about 30 wt %, or at least about 40 wt %, or at least about 50 wt %, or at least about 60 wt %, or even about 70 wt % of nanomagnetic particles, relative to the total mass of the beads.

The nanomagnetic particle content that is to be incorporated in the beads will generally be dictated by the intended application of the beads. For example, where the beads are to be used for providing hyperthermia therapy, or as synonymously used herein hyperthermic treatment, those skilled in the art will appreciate that the volumetric absorption rate (VAR) of the beads should be sufficient under appropriate magnetic field conditions to promote therapeutic heating at a target site. Generally, the VAR of such beads will be at least about 1 Watts/cm$^3$, preferably at least about 10 Watts/cm$^3$, when exposed to a magnetic field of a clinically acceptable frequency and strength.

As used herein, "VAR" is intended to define the heating quality of the polymer microgel beads and is expressed as the amount of heat released by a unit volume of the bead per unit time during exposure to a magnetic field of a defined frequency and field strength.

In terms of the nanomagnetic particle content of the polymer microgel beads, those skilled in the art will appreciate that the ratio of the polymeric matrix of the beads to the nanomagnetic particles can potentially influence the heating efficiency of the beads. For example, as the nanomagnetic particle content of the beads increases there may be a greater potential for the particles to aggregate and thus reduce the effective VAR of the beads. However, the polymer microgel beads in accordance with the invention can advantageously be prepared using a relatively high nanomagnetic particle content with little or no aggregation of the particles. Accordingly, the heating quality of the beads can be maximised for a given nanomagnetic particle content.

The "nanomagnetic particles" used in accordance with the invention are of a size of less than 1 micron. Those skilled in the art will appreciate that the composition and/or size of the particles can influence their magnetic properties. The nanomagnetic particles will generally exhibit ferromagnetic, ferrimagnetic or superparamagnetic properties.

The specific size of the nanomagnetic particles used will generally be dictated by the intended application of the polymer microgel beads. For some applications, it may be desirable for the nanomagnetic particles to be of a size of less than about 500 nm, for example less than about 100 nm, or less than about 50 nm. The method of the present invention has been found to be particularly well suited to producing polymer beads incorporating nanomagnetic particles having a size ranging from about 1 nm to about 40 nm.

Where the polymer microgel beads are to be used for providing hyperthermic treatment, the nanomagnetic particles used will generally have a particle size of less than about 50 nm, for example ranging from about 1 nm to about 40 nm.

There is no particular limitation on the type of nanomagnetic particles that may be used in accordance with the invention. Examples of suitable magnetic materials include, but are not limited to, iron, nickel, chromium, cobalt, oxides thereof or mixtures of any of these. Preferred iron oxide magnetic materials include $\gamma$-ion oxide (i.e. $\gamma$-$Fe_2O_3$, also known as maghemite) and magnetite ($Fe_3O_4$).

In some applications, it may be desirable that the polymer microgel beads incorporate nanomagnetic particles that are superparamagnetic (i.e. nano-superparamagnetic particles). As used herein, the term "superparamagnetic" is intended to mean magnetic particles that do not have the following properties; (i) coercivity, (ii) remanence, or (iii) a hysteresis loop when the rate of change of an applied magnetic field is quasi static.

Those skilled in the art will appreciate that the VAR of superparamagnetic particles is proportional to the quadrature component of the complex susceptibility, i.e. $\chi$". Maximum VAR is obtained when the Néel relaxation time, $\tau_N$, is equal to the inverse of the magnetic field frequency, $\omega$, i.e.

$$\tau_N \omega = 1.$$

In turn, $\tau_N$ is determined by the magnetic anisotropy energy, KV, where K is the magnetic anisotropy and V is the particle volume. The value of K is determined by magnetocrystalline anisotropy or the particle shape if it is not perfectly spherical. This assumes particles are smaller than the critical size for formation of magnetic domains, i.e. they are in the superparamagnetic regime.

The properties of VAR, magnetic susceptibility, magnetic moment and saturation magnetization are measurable by standard methods known to those skilled in the art.

The nanomagnetic particles may be selected from ferrites of general formula $MO.Fe_2O_3$ where M is a bivalent metal such as Fe, Co, Ni, Mn, Be, Mg, Ca, Ba, Sr, Cu, Zn, Pt or mixtures thereof, or magnetoplumbite type oxides of the general formula $MO.6Fe_2O_3$ where M is a large bivalent ion, metallic iron, cobalt or nickel. Additionally, they could be particles of pure Fe, Ni, Cr or Co or oxides of these. Alternatively they could be mixtures of any of these.

In one embodiment, the nanomagnetic particles are particles of iron oxide such as magnetite ($Fe_3O_4$) or maghemite ($\gamma$-$Fe_2O_3$) with a particle size preferably less than 50 nanometers, for example between 10 and 40 nanometers.

In a further embodiment, the nanomagnetic particles are particles of maghemite. Such particles can provide a number of advantages in that maghemite nano particles of optimum size possess a higher VAR than do optimum size magnetite nano particles when subjected to clinically relevant magnetic field conditions, and maghemite is generally a more chemical stable form of iron oxide than magnetite.

Those skilled in the art will appreciate that the higher VAR of maghemite means that a lower nanomagnetic particle content can be used to produce the polymer microgel beads with the required VAR.

Nanomagnetic particles used in accordance with the invention may be conveniently prepared using techniques known in the art.

In accordance with a method of the invention, there is provided a dispersion comprising a continuous organic phase and a dispersed aqueous phase. Those skilled in the art may commonly refer to such a dispersion as an inverse emulsion or a water in oil dispersion. The dispersion used in accordance with the invention may therefore simplistically be described as an organic liquid having droplets of aqueous liquid dispersed therein. The term "phase" is therefore used herein to simply convey that there is an interface between the organic and aqueous liquids formed as a result of the liquids being substantially immiscible.

In isolation, it will be appreciated that organic and aqueous phases will in effect be an organic and aqueous liquid, respectively. In other words, the term phase simply assists with describing these liquids when provided in the form of a dispersion. However, for convenience, the organic and aqueous liquids used to prepare the dispersion may hereinafter simply be referred to as the organic and aqueous phases, respectively. It may also be convenient to refer to the organic and aqueous liquids as organic and aqueous solvents, respectively.

The organic phase will generally comprise or be a hydrophobic liquid. Suitable hydrophobic liquids include, but are not limited to, one or more water-insoluble aliphatic or aromatic organic liquids, such as, for example, hydrocarbons having 6 to 20 carbon atoms, kerosene, petrolatums, xylene, toluene, branched-chain isoparaffins and mixtures thereof.

Apart from the dispersed aqueous phase, the continuous organic phase may comprise one or more additives typically employed in the art. For example, it may be necessary to employ a dispersing agent in order to facilitate maintaining the aqueous phase in a dispersed state throughout the continuous organic phase. Those skilled in the art will be able to select a suitable dispersing agent for this purpose.

Suitable dispersing agents will generally be any surfactant that can stabilise the dispersed aqueous phase throughout the continuous organic phase. The dispersing agent is typically added to the organic phase, but can be added to the aqueous phase depending on the solubility of the agent used.

Representatives of such dispersing agents include, but are not limited to, non-ionic surfactants, sorbitan fatty acid esters such as, for example, sorbitan monooleate and sorbitan monolaurate, glycerol esters such as, for example, glycerol monooleate and glycerol monoricinoleate, phthalic esters, partial fatty acid esters of polyglycerol, the reaction product of oleic acid with isopropanolamide, 12-hydroxystearic acid-polyethylene glycol block copolymers (commercially available as Hypermer B246 and Hypermer B261), fatty acid glycerides, glycerin esters, as well as ethoxylated derivatives thereof; cationic surfactants including, but are not limited to, ammonium salts, such as distearyl dimethyl ammonium chloride and dioleyl dimethyl ammonium dichloride; and anionic surfactants such as bis-tri-decyl sulfosuccinic acid salt; or mixtures thereof.

Polymeric dispersing agents are generally preferred, and may be selected from 12-hydroxystearic acid-polyethylene glycol block copolymers, poly(isobutylene) succinic hydride diethylethanol amine (PIBSADEEA), ethylene-co-maleic anhydride, poly(alpha-olefin-co-maleic anhydride), cellulose ethers such as ethyl cellulose, methyl cellulose, hydroxyethyl cellulose, hydroxypropyl cellulose, and carboxyethyl cellulose, poly(lauryl methacrylate-co-acrylic acid), cellulose esters such as acetates, propylonates and butyrates.

The dispersing agents can be used alone or in combination. The dispersing agent is employed in an amount sufficient to maintain the dispersion during polymerization. The amount and type of dispersing agent(s) employed will vary depending on the composition of the organic and aqueous phases. Those skilled in the art will be able to select a suitable agent(s) and its amount for a given dispersion. Generally, the dispersing agent is employed in an amount not of greater than about 5 wt. % of the total dispersion.

A more detailed discussion concerning the dispersed aqueous phase is provided below, but in general terms it will be appreciated that the aqueous phase will be substantially immiscible in the organic phase. The aqueous phase will of course comprise water, and may also comprise one or more hydrophilic liquids such as methanol, ethanol, dioxane and the like. By "hydrophilic liquid" is meant a liquid that is miscible with water.

The dispersion used in accordance with the invention may be prepared using techniques well known in the art. For example, a suitable aqueous liquid may be combined with a suitable organic liquid and subjected to agitation, for example, by some shearing means. As indicated above, a dispersing agent may also be used to facilitate maintaining the resulting aqueous phase in a dispersed state throughout the resulting continuous organic phase. Through the appropriate control of this process, the size of the dispersed aqueous phase droplets can be selected so as to tailor the size of the polymer microgel beads formed in accordance with the method.

The dispersed aqueous phase comprises one or more ethylenically unsaturated monomers that are soluble in the aqueous phase. Such monomers can therefore be classified as having hydrophilic character. It will be appreciated that polymerisation of these monomers gives rise to the crosslinked three dimensional polymer chain network of the polymer microgel beads. Polymerisation of the monomers will generally occur through free radical polymerisation of the unsaturated bonds present in the monomers. Those skilled in the art will appreciate that in order to provide for the crosslinked polymeric matrix of the polymer microgel beads, at least some of the ethylenically unsaturated monomers present in the aqueous phase must be multi-ethylenically unsaturated monomers (i.e. ethylenically unsaturated monomers having two or more double bonds).

The specific form of the polymeric matrix of the polymer microgel beads may be conveniently tailored through variation of the concentration of ethylenically unsaturated monomers present in the aqueous phase and also through variation of the ratio of monoethylenically unsaturated monomers to multi-ethylenically unsaturated monomers. The polymeric matrix may also of course be varied through the selection of specific ethylenically unsaturated monomers.

Accordingly, the polymer microgel beads may be prepared such that they have a relatively low crosslinked density so as to be more readily swollen by an aqueous medium, or such that hey have a relatively high crosslinked density so as to be less readily swollen by an aqueous medium. The amount and type of ethylenically unsaturated monomers included in the aqueous phase will generally be dictated by the intended application for the polymer microgel beads. For example, if the application requires the beads to have a relatively low nanomagnetic particle content, then the amount of ethylenically unsaturated monomers included in the aqueous phase will be higher than if the beads were to have a relatively high nanomagnetic particle content.

In order to provide for the crosslinked three dimensional polymer chain network of the polymer microgel beads, the ethylenically unsaturated monomers present in the aqueous phase will generally comprise about 5 mole % to about 15 mole % of multi-ethylenically unsaturated monomers.

Suitable ethylenically unsaturated monomers that may be included in the aqueous phase are those having sufficient hydrophilic character so as to be soluble or miscible in the aqueous phase. Polymers formed from monoethylenically unsaturated monomers of this type will also generally be soluble in the aqueous phase. Accordingly, a proportion of multi-ethylenically unsaturated monomers will generally need to be present in order to "fix" the resulting polymeric matrix such that it can not be fully solvated by the aqueous phase (i.e. the polymeric matrix is required to be insoluble in but can be swollen by the aqueous phase).

Suitable monoethylenically unsaturated monomers that may be used in the dispersed aqueous phase include, but are not limited to, acrylic acid, methacrylic acid, hydroxyethyl methacrylate, hydroxypropyl methacrylate, acrylamide and methacrylamide, hydroxyethyl acrylate, N-methylacrylamide, dimethylaminoethyl methacrylate, itaconic acid, p-styrene carboxylic acids, p-styrene sulfonic acids, vinyl sulfonic acid, vinyl phosphonic acid, ethacrylic acid, alpha-chloroacrylic acid, crotonic acid, fumaric acid, citraconic acid, mesaconic acid, maleic acid, 2-(dimethyl amino) ethyl and propyl acrylates and methacrylates, and the corresponding 3-(diethylamino) ethyl and propyl acrylates and methacrylates.

Suitable multi-ethylenically unsaturated monomers that may also be used in the dispersed aqueous phase to afford crosslinks in the polymeric matrix of the polymer microgel beads include, but are not limited to, ethylene glycol di(meth)acrylate, triethylene glycol di(meth)acrylate, tetraethylene glycol di(meth)acrylate, 1,3-butylene glycol di(meth)acrylate, trimethylolpropane tri(meth)acrylate, 1,4-butanediol di(meth)acrylate, neopentyl glycol di(meth)acrylate, 1,6-hexanediol di(meth)acrylate, pentaerythritol di(meth)acrylate, pentaerythritol tri(meth)acrylate, pentaerythritol tetra (meth)acrylate, glycerol di(meth)acrylate, glycerol allyloxy di(meth)acrylate, 1,1,1-tris(hydroxymethyl)ethane di(meth) acrylate, 1,1,1-tris(hydroxymethyl)ethane tri(meth)acrylate, 1,1,1-tris(hydroxymethyl)propane di(meth)acrylate, 1,1,1- tris(hydroxymethyl)propane tri(meth)acrylate, triallyl cyanurate, triallyl isocyanurate, triallyl trimellitate, diallyl phthalate, diallyl terephthalate, divinyl benzene, methylol (meth)acrylamide, triallylamine, oleyl maleate, glyceryl propoxy triacrylate, allyl methacrylate, and methylenebis (meth) acrylamide.

The dispersed aqueous phase also comprises the nanomagnetic particles dispersed therein. Thus, it will be appreciated that the nanomagnetic particles are in effect also dispersed throughout the one or more ethylenically unsaturated monomers, which, together with the aqueous solvent, collectively form the aqueous phase dispersed throughout the continuous organic phase. Each dispersed droplet of aqueous phase therefore comprises a substantially uniform distribution of the monomer and the nanomagnetic particles.

Polymerisation of the monomers therefore provides for the polymer microgel beads having a size that is primarily determined by the size of the dispersed aqueous phase droplets, and also having nanomagnetic particles substantially uniformly distributed throughout the entire bead.

In order to provide the polymer microgel beads with a substantially uniform distribution of the nanomagnetic particles throughout the polymeric matrix of each bead, the nanomagnetic particles are dispersed throughout the aqueous phase. The nanomagnetic particles are maintained in their dispersed state during polymerisation by a steric stabiliser. The steric stabiliser is a polymeric material in its own right and comprises a steric stabilising polymeric segment and an anchoring polymeric segment. The steric stabilising polymeric segment is different from the anchoring polymeric segment, and the anchoring polymeric segment has an affinity toward the surface of the nanomagnetic particles and secures the stabiliser to the particles.

Without wishing to be limited by theory, it is believed that the steric stabiliser used in accordance with the invention forms a strong association with the nanomagnetic particles and provides for a particularly stable dispersion of the particles throughout the aqueous phase. The strong association between the particles and the steric stabiliser is believed to result from the polymeric nature of the anchoring segment of the stabiliser which provides multiple sites for binding interactions between the segment and the particles. The steric stabilising polymeric segment of the stabiliser is believed to promote effective and efficient stabilisation of the particles by providing steric repulsion forces.

The steric stabiliser used in accordance with the invention has been found to be particularly effective at stabilising relatively small nanomagnetic particles (i.e. less than about 100 nm in size) throughout the aqueous phase. In particular, the stabiliser has been found to effectively and efficiently stabilise relatively small nanomagnetic particles in a substantially non-aggregated form throughout the aqueous phase. By virtue of this effective and efficient form of stabilisation, the polymer microgel beads may be prepared in accordance with the invention with a relatively high nanomagnetic particle content (e.g. up to about 80 wt. %) while still maintaining a substantially uniform and non-aggregated distribution of the nanomagnetic particles.

As part of the aqueous phase composition, the nanomagnetic particles are maintained in their dispersed state by a steric stabiliser. By being "maintained" in this context is meant that in the absence of the steric stabiliser the nanomagnetic particles would otherwise flocculate or settle out from the aqueous phase as sediment. In other words, the steric stabiliser functions to retain the nanomagnetic particles in the dispersed state to afford a stable dispersion. In this context, a "stable" dispersion is considered to be one in which the dispersed nanomagnetic particles does not aggregate to an undesirable extent over the time frame of performing the polymerisation.

In accordance with the invention, a steric stabiliser functions to maintain the nanomagnetic particles in the dispersed state. By being a "steric" stabiliser is meant that stabilisation of the nanomagnetic particles throughout the aqueous phase occurs as a result of steric repulsion forces. Having said this, the steric stabiliser may present electrostatic repulsion forces that also assist with stabilisation of the nanomagnetic particles.

The steric stabiliser used in accordance with the invention has a polymeric composition. There is no particular limitation on the molecular weight of the steric stabiliser, and this feature of the stabiliser may be dictated in part by the nature of the nanomagnetic particles that it is destined to stabilise. Generally, the steric stabiliser will have a number average molecular weight of less than about 50,000.

In some embodiments of the invention, it may be preferable that the number average molecular weight of the steric stabiliser is less than about 30,000, or less than about 20,000, or less than about 10,000 or even less than about 5,000. The number average molecular weight of the steric stabiliser may also range from about 1,000 to about 3,000.

Steric stabilisers used in accordance with the invention having a relatively low number average molecular weight (e.g. less than about 5,000, preferably in the range of from about 1,000 to about 3,000) have been found to be particularly effective at stabilising relatively small nanomagnetic particles (i.e. particles of less than about 100 nm in size).

Molecular weight values defined herein are those determined using gel permeation chromatography (GPC).

The amount of steric stabiliser used relative to the nanomagnetic particles will vary depending on the nature of the particles, particularly their size. For example, 1 g of 5 nm nanomagnetic particles will require more stabiliser than 1 g of 1 micron nanomagnetic particles due to their increased surface area. Those skilled in the art will be able to determine the required amount of stabiliser for the selected nanomagnetic particles.

The steric stabiliser used in accordance with the invention is a polymeric material that may be prepared by any suitable polymerisation technique.

In one embodiment at least one of the steric stabilising and anchoring polymeric segments that make up the steric stabiliser are derived from one or more ethylenically unsaturated monomers that have been polymerised by a living polymerisation technique. Employing at least one such segment is believed to enhance the stabilising properties of the steric stabiliser. Further detail regarding suitable living polymerisation techniques is discussed below. Where only one of the segments is derived in this manner, the other segment may be derived by any other conventional polymerisation technique known by those skilled in the art.

By "steric stabilising polymeric segment" is meant a segment or region of the steric stabiliser that is polymeric (i.e. formed by the polymerisation of at least one type of monomer) and that provides for the steric stabilising function of the steric stabiliser. For convenience, the steric stabilising polymeric segment may herein after be referred to polymeric segment "A".

As alluded to above, the steric stabilising polymeric segment functions to stabilise the nanomagnetic particles throughout the aqueous phase by providing steric repulsion forces.

By being polymeric, it will be appreciated that the steric stabilising segment comprises polymerised monomer residues. Thus, the segment will comprise polymerised monomer residues that give rise to the required steric stabilising properties. The polymerised monomer residues that make up the steric stabilising polymeric segment may be the same or different.

The steric stabilising polymeric segment may be substituted with a moiety (e.g. an optional substituent as herein defined), or contain a polymerised monomer residue, that gives rise to electrostatic stabilising properties.

In order to provide the desired steric stabilising effect, the steric stabilising polymeric segment will of course be soluble in the aqueous phase. Determining the solubility of a given steric stabilising polymeric segment in a given aqueous solvent can readily be determined by simply preparing the polymeric segment in isolation and conducting a suitable solubility test in the chosen aqueous solvent.

The steric stabiliser as a whole, may or may not be soluble in the chosen aqueous solvent, but will none the less present a steric stabilising polymeric segment that is.

Those skilled in the art will have an understanding of polymeric materials that may be employed as the steric stabilising polymeric segment, as to the monomers that may be polymerised to form such polymers. For example, suitable polymeric materials include, but are not limited to, polyacrylamide, polyethylene oxide, polyhydroxyethylacrylate, poly N-isopropylacrylamide, polydimethylaminoethylmethacrylate, polyvinyl pyrrolidone and copolymers thereof. Thus, suitable monomers that may be used to form the stabilising polymeric segment include, but are not limited to, acrylamide, ethylene oxide, hydroxyethylacrylate, N-isopropylacrylamide, dimethylaminoethylmethacrylate, vinyl pyrrolidone and combinations thereof.

By being able to select a specific steric stabilising polymeric segment independent of the anchoring polymeric segment, the steric stabilisers used in accordance with the invention can advantageously be tailor designed to suit a particular aqueous phase and thereby maximise the steric stabilising properties of the steric stabiliser.

Although there is no particular limitation on the polymerisation technique that may be used to prepare the steric stabilising segment, a living polymerisation technique can afford a number of advantages. Those skilled in the art will appreciate that "living polymerisation" is a form of addition polymerisation whereby chain growth propagates with essentially no chain transfer and essentially no termination that give rise to dead polymer chains. By a "dead polymer chain" is meant one that can not undergo further addition of monomers.

In a living polymerization, typically all polymer chains are initiated at the start of the polymerization with minimal new chains being initiated in latter stages of the polymerization. After this initiation process, all the polymer chains in effect grow at the same rate. Characteristics and properties of a living polymerization generally include (i) the molecular weight of the polymer increases with conversion, (ii) there is a narrow distribution of polymer chain lengths (i.e. they are of similar molecular weight), and (iii) additional monomers can be added to the polymer chain to create block co-polymer structures. Thus living polymerisation enables excellent control over molecular weight, polymer chain architecture and polydispersity of the resulting polymer that can not be achieved with non-living polymerization methods.

Suitable living polymerisation techniques may be selected from ionic polymerisation and controlled radical polymerisation (CRP). Examples of CRP include, but are not limited to, iniferter polymerisation, stable free radical mediated polymerisation (SFRP), atom transfer radical polymerisation (ATRP), and reversible addition fragmentation chain transfer (RAFT) polymerisation.

Living ionic polymerisation is a form of addition polymerisation whereby the kinetic-chain carriers are ions or ion pairs. The polymerisation proceeds via anionic or cationic kinetic-chain carriers. In other words, the propagating species will either carry a negative or positive charge, and as such there will also be an associated counter cation or counter anion, respectively. For example, in the case of anionic polymerisation, the polymerisation may be conducted using a moiety represented as $I^-M^+$, where I represents an organo-anion (e.g. an optionally substituted alkyl anion) and M represents an associated countercation, or in the case of living cationic polymerisation, the moiety might be represented as $I^+M^-$, where I represents an organo-cation (e.g. an optionally substituted alkyl cation) and M represents an associated counteranion. Suitable moieties for conducting anionic and cationic living polymerisation are well known to those skilled in the art.

The living polymerisation technique may be a CRP technique.

Iniferter polymerisation is a well known form of CRP, and is generally understood to proceed by a mechanism illustrated below in Scheme 1.

Scheme 1: General mechanism of controlled radical polymerisation with iniferters.

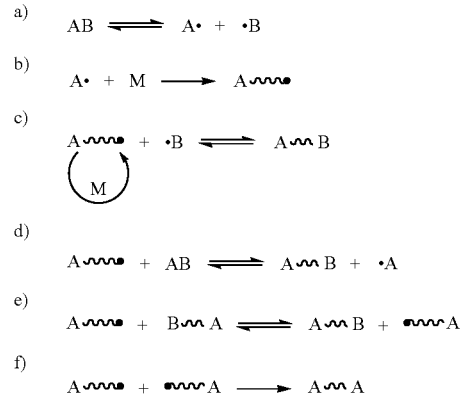

With reference to Scheme 1, the iniferter AB dissociates chemically, thermally or photochemically to produce a reactive radical species A and generally a relatively stable radical species B (for symmetrical iniferters the radical species B will be the same as the radical species A) (step a). The radical species A can initiate polymerisation of monomer M (in step b) and may be deactivated by coupling with radical species B (in step c). Transfer to the iniferter (in step d) and/or transfer to dormant polymer (in step e) followed by termination (in step f) characterise iniferter chemistry.

Suitable moieties for conducting iniferter polymerisation are well known to those skilled in the art, and include, but are not limited to, dithiocarbonate, disulphide, and thiuram disulphide moieties.

SFRP is a well known form of CRP, and is generally understood to proceed by a mechanism illustrated below in Scheme 2.

Scheme 2: General mechanism of controlled radical polymerisation with stable free radical mediated polymerisation.

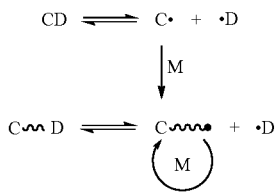

With reference to Scheme 2, SFRP moiety CD dissociates to produce an active radical species C and a stable radical species D. The active radical species C reacts with monomer M, which resulting propagating chain may recombine with the stable radical species D. Unlike iniferter moieties, SFRP moieties do not provide for a transfer step.

Suitable moieties for conducting SFRP are well known to those skilled in the art, and include, but are not limited to, moieties capable of generating phenoxy and nitroxy radicals. Where the moiety generates a nitroxy radical, the polymerisation technique is more commonly known as nitroxide mediated polymerisation (NMP).

Examples of SFRP moieties capable of generating phenoxy radicals include those comprising a phenoxy group substituted in the 2 and 6 positions by bulky groups such as tert-alkyl (e.g. t-butyl), phenyl or dimethylbenzyl, and optionally substituted at the 4 position by an alkyl, alkyloxy, aryl, or aryloxy group or by a heteroatom containing group (e.g. S, N or O) such dimethylamino or diphenylamino group. Thiophenoxy analogues of such phenoxy containing moieties are also contemplated.

SFRP moieties capable of generating nitroxy radicals include those comprising the substituent $R^1R^2N-O-$, where $R^1$ and $R^2$ are tertiary alkyl groups, or where $R^1$ and $R^2$ together with the N atom form a cyclic structure, preferably having tertiary branching at the positions α to the N atom. Examples of such nitroxy substituents include 2,2,5,5-tetraalkylpyrrolidinoxyl, as well as those in which the 5-membered hetrocycle ring is fused to an alicyclic or aromatic ring, hindered aliphatic dialkylaminoxyl and iminoxyl substituents. A common nitroxy substituent employed in SFRP is 2,2,6,6-tetramethyl-1-piperidinyloxy.

ATRP is a well known form of CRP, and generally employs a transition metal catalyst to reversibly deactivate a propagating radical by transfer of a transferable atom or group such as a halogen atom to the propagating polymer chain, thereby reducing the oxidation state of the metal catalyst as illustrated below in Scheme 3.

Scheme 3: General mechanism of controlled radical polymerisation with atom transfer radical polymerisation.

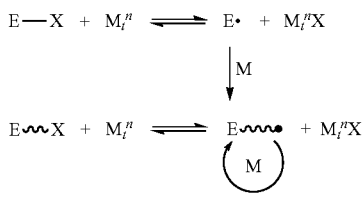

With reference to Scheme 3, a transferable group or atom (X, e.g. halide, hydroxyl, $C_1$-$C_6$-alkoxy, cyano, cyanato, thiocyanato or azido) is transferred from the organic compound (E) (e.g. optionally substituted alkyl, optionally substituted aryl, optionally substituted alkylaryl, or the polymer chain) to a transition metal catalyst ($M_t$, e.g. copper, iron, gold, silver, mercury, palladium, platinum, cobalt, manganese, ruthenium, molybdenum, niobium, or zinc) having oxidation number (n), upon which a radical species is formed that initiates polymerisation with monomer (M). As part of this process, the metal complex is oxidised ($M_t^{n+1}X$). A similar reaction sequence is then established between the propagating polymer chain and the dormant X end-capped polymer chains.

RAFT polymerisation is well known in the art and is believed to operate through the mechanism outlined below in Scheme 4.

Scheme 4: General mechanism of controlled radical polymerisation with reversible addition fragmentation chain transfer polymerisation.

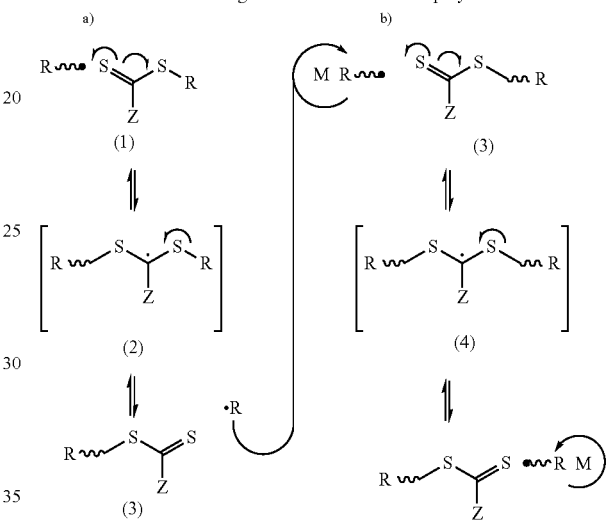

With reference to Scheme 4, RAFT polymerisation is believed to proceed through initial reaction sequence (a) that involves reaction of a RAFT moiety (1) with a propagating radical. The labile intermediate radical species (2) that is formed fragments to form a temporarily deactivated dormant polymer species (3) together a radical (R) derived from the RAFT moiety. This radical can then promote polymerisation of monomer (M), thereby reinitiating polymerisation. The propagating polymer chain can then react with the dormant Polymer species (3) to promote the reaction sequence (b) that is similar to reaction sequence (a). Thus, a labile intermediate radical (4) is formed and subsequently fragments to form again a dormant polymer species together with a radical which is capable of further chain growth.

RAFT moieties generally comprise a thiocarbonylthio group (which is a divalent moiety represented by: —C(S)S—) and include xanthates, dithioesters, dithiocarbonates, dithiocarbanates and trithiocarbonates.

The steric stabilising polymeric segment may be formed by the polymerisation of one type of monomer or a combination of two or more different monomers. Accordingly, the steric stabilising polymeric segment may be a homopolymeric segment or a copolymeric segment.

Given that the stabilising polymeric segment forms only part of the steric stabiliser, rather than defining the steric stabilising polymeric segment in terms of its number average molecular weight, it can instead be useful to make reference to the number of polymerised monomeric units that collectively form the segment. Thus, although there is no particular limitation on the number of such units that collectively form the steric stabilising polymeric segment, in some embodiments of the invention it may be desirable that the steric stabiliser has a relatively low number average molecular weight. In that case, it is preferable that the steric stabilising polymeric segment has less than about 50, more preferably less than about 40, most preferably from about 15 to about 30 polymerised monomer residue repeat units that make up the overall segment.

By an "anchoring polymeric segment" is meant a segment or region of the steric stabiliser that is polymeric and that has an affinity toward the surface of the nanomagnetic particles and functions to secure the steric stabiliser to the particles. For convenience, the anchoring polymeric segment may hereinafter be referred to as polymeric segment "B".

By being polymeric, it will be appreciated that the anchoring segment comprises polymerised monomer residues. In particular, the segment will comprise polymerised monomer residues that give rise to the required binding affinity toward the nanomagnetic particles. The polymerised monomer residues that make up the anchoring polymeric segment may be the same or different.

It is believed that the ability of the anchoring segment to present multiple sites for binding interactions with the nanomagnetic particles at least in part gives rise to the excellent stabilising properties provided by the steric stabiliser.

Generally, the anchoring segment will have at least two polymerised monomer residues that each provides a site for binding with the nanomagnetic particles, preferably at least three, more preferably at least five, still more preferably at least seven, most preferably at least ten of such polymerised monomer residues. Not all of the polymerised monomer residues that make up the anchoring segment are necessarily required to give rise to a binding interaction with the particles, but it is generally preferred that the majority if not all of the polymerised monomer residues that make up the anchoring segment do give rise to a binding interaction with the particles.

The anchoring segment may therefore be described as having multiple sites that collectively secure the stabiliser to the particulate material.

The anchoring polymeric segment can also be substituted with a moiety (e.g. an optional substituent as herein defined) that may or may not give rise to a binding interaction with the nanomagnetic particles.

In order to provide the desired anchoring effect, the anchoring polymeric segment will have a binding affinity toward the nanomagnetic particles. The specific mode by which the anchoring segments bind to the particles is not particularly important, for example it might be by way of electrostatic forces, hydrogen bonding, ionic charge, Van der Waals forces, or any combination thereof. A particular advantage provided by the anchoring polymeric segment is that it can provide multiple sites for binding interactions with the particles. Thus, even where a given binding site only provides a relatively weak interaction with the particles, the presence of multiples of such sites within the segment enables it as a whole to bind securely with the particles.

The specific anchoring polymeric segment required will generally be dictated to the nature of the nanomagnetic particles to which it is to bind. When describing the interaction of the anchoring polymeric segment with the particles, it can be convenient to refer to the hydrophilic and hydrophobic character of the segment and the particles. Thus, in general, suitable binding interactions will occur when the segment and the particles have similar hydrophilic or hydrophobic character. For example, where the particles have a relatively hydrophilic surface (e.g. its surface can be wetted with an aqueous solution), then good binding should be attained using an anchoring polymeric segment that has hydrophilic character (e.g. in its isolated form the segment would be soluble in an aqueous medium). Such an example might be realised where the particles are of a type that can form a charge on their surface. In that case, it may be desirable for the segment to comprise polymerised residues of monomers that can also form a charge (e.g. residues of an ionisable monomer) so as to promote ionic binding between the segment and the particles. Promoting the formation of such charged species might be facilitated by adjusting the pH of the aqueous phase in which the stabiliser and particles reside.

Nanomagnetic particles used in accordance with the invention will generally have a relatively hydrophilic surface, and may be capable of forming a charge on their surface. In that case, the anchoring polymeric segment will preferably comprise polymerised residues of an ionisable monomer.

By the term "ionisable monomer" is meant that the monomer comprises a functional group which can be ionised in solution to form a cationic or anionic group. Such functional groups will generally be capable of being ionised under acidic or basic conditions through loss or acceptance of a proton. Generally, the functional groups are acid groups or basic groups. For example, a carboxylic acid functional group may form a carboxylate anion under basic conditions, and an amine functional group may form a quaternary ammonium cation under acidic conditions. The functional groups may also be capable of being ionised through an ion exchange process.

Examples of suitable ionisable monomers having acid groups include, but are not limited to, methacrylic acid, acrylic acid, itaconic acid, p-styrene carboxylic acids, p-styrene sulfonic acids, vinyl sulfonic acid, vinyl phosphonic acid, monoacryloxyethyl phosphate, 2-(methacryloyloxy) ethyl phosphate, ethacrylic acid, alpha-chloroacrylic acid, crotonic acid, fumaric acid, citraconic acid, mesaconic acid, and maleic acid. Examples of suitable ionisable monomers which have basic groups include, but are not limited to, 2-(dimethyl amino) ethyl and propyl acrylates and methacrylates, and the corresponding 3-(diethylamino) ethyl and propyl acrylates and methacrylates.

Those skilled in the art will be able to select an appropriate anchoring polymeric segment to bind with the surface of the selected nanomagnetic particles.

By being able to select a specific anchoring polymeric segment independent of the steric stabilising polymeric segment, the steric stabilisers used in accordance with the invention can advantageously be tailor designed to suit particular nanomagnetic particles and thereby maximise the anchoring properties of the steric stabiliser.

Those skilled in the art will appreciate the variety of polymeric materials that may be employed as the anchoring polymeric segment, as to the monomers that may be polymerised to form such polymers. For example, suitable polymeric materials include, but are not limited to, polyacrylic acid, polymethacrylic acid, polystyrene, polyitaconic acid, poly-p-styrene carboxylic acids, poly-p-styrene sulfonic acids, polyvinyl sulfonic acid, polyvinyl phosphonic acid, poly monoacryloxyethyl phosphate, poly-2-(methylacryloyloxy) ethyl phosphate, polyethacrylic acid, poly-alpha-chloroacrylic acid, polycrotonic acid, polyfumaric acid, polycitraconic acid, polymesaconic acid, polymaleic acid, poly-2-(dimethyl amino) ethyl and propyl acrylates and methacrylates, the corresponding poly-3-(diethylamino) ethyl and propyl acrylates and methacrylates, hydrophobic acrylate and methacrylate polymers, polydimethylaminoethylmethacrylate, and copolymers thereof. Thus, suitable monomers that may be used to form the anchoring polymeric segment include, but are not limited to, acrylic acid, methacrylic acid, itaconic acid, p-styrene carboxylic acids, p-styrene sulfonic acids, vinyl sulfonic acid, vinyl phosphonic acid, monoacryloxyethyl phosphate, 2-(methylacryloyloxy) ethyl phosphate, ethacrylic acid, alpha-chloroacrylic acid, crotonic acid, fumaric acid, citraconic acid, mesaconic acid, maleic acid, 2-(dimethyl amino) ethyl and propyl acrylates and methacrylates, the corresponding 3-(diethylamino) ethyl and propyl acrylates and methacrylates, styrene, hydrophobic acrylate and methacrylate monomers, dimethylaminoethylmethacrylate, and combinations thereof.

There is no particular limitation on the polymerisation technique that may be used to prepare the anchoring polymeric segment. Living polymerisation techniques such as those herein described have been found particularly useful in preparing the anchoring polymeric segment. Where at least one of the steric stabilising and anchoring polymeric segments are derived from one or more ethylenically unsaturated monomers that have been polymerised by a living polymerisation technique, it will preferably be the anchoring segment.

In one embodiment, both the steric stabilising and anchoring polymeric segments are derived from one or more ethylenically unsaturated monomers that have been polymerised by a living polymerisation technique.

The anchoring polymeric segment may be formed by the polymerisation of one type of monomer or a combination of two or more different monomers. Accordingly, the anchoring polymeric segment may be a homopolymeric segment or a copolymeric segment.

Given that the anchoring polymeric segment forms only part of the steric stabiliser, rather than defining the anchoring polymeric segment in terms of its number average molecular weight, it can instead be useful to make reference to the number of polymerised monomeric units that collectively form the segment. Thus, although there is no particular limitation on the number of such units that collectively form the anchoring polymeric segment, in some embodiments of the invention it may be desirable that the steric stabiliser has a relatively low number average molecular weight. In that case, it is preferable that the anchoring polymeric segment has less than about 50, more preferably less than about 40, still more preferably less than about 30, even more preferably from about 5 to about 25, most preferably from about 5 to about 15 polymerised monomer residue repeat units that make up the overall segment.

Provided that the stabiliser functions as herein described there is no particular limitation on how the stabilising polymeric segment and the anchoring polymeric segment are to be spatially arranged.

The steric stabilising polymeric segment and the anchoring polymeric segment may be coupled to each other by any suitable means to form the steric stabiliser used in accordance with invention. For example, the steric stabiliser may be described as or comprising the structure A-C—B, where A represents the steric stabilising polymeric segment, B represents the anchoring polymeric segment and C represents a coupling moiety. Alternatively, the steric stabilising polymeric segment and the anchoring polymeric segment may be directly coupled to each other via a covalent bond and therefore the stabiliser can be simplistically described as or comprising an A-B block copolymer. In that case, A represents the steric stabilising polymeric segment and B represents the anchoring polymeric segment. It will be appreciated from the description above that each of A and B can independently be a homopolymer or a copolymer (e.g. random, block, tapered, etc.).

The stabiliser may comprise more than one steric stabilising polymeric segment (A) and more than one anchoring polymeric segment (B). For example, the stabiliser may be described as or comprising an A-B-A block copolymer. In that case, each A represents the steric stabilising polymeric segment, which may be the same or different, and B represents the anchoring polymeric segment. The stabiliser might also be described as or comprising a B-A-B block copolymer, where each B represents the anchoring polymeric segment, which may be the same or different, and A represents the steric stabilising polymeric segment that is of sufficient chain length such that it forms a "loop" that extends into the aqueous phase and performs its stabilising role.

The stabiliser may also have more complex structures such as star and comb polymer structures. In that case, the anchoring polymeric segment B might represent the main polymer backbone of such structures, with multiple steric stabilising polymeric segments A being attached thereto.

The interaction of a steric stabiliser used in accordance with the invention (in the form of an A-B block copolymer structure) with a nanomagnetic particle in the aqueous phase might be illustrated in the not to scale simplified schematic shown in FIG. 1.

With reference to FIG. 1, the steric stabiliser represented by an A-B block copolymer exhibits an affinity toward the surface of the nanomagnetic particle (P) through the anchoring polymeric segment (B). The anchoring polymeric segment (B) therefore secures the steric stabiliser to the particle. The anchoring polymeric segment (B) provides multiple sites for binding interactions between the segment and the particle. The steric stabilising polymeric segment (A), which is different to segment (B), is soluble in the aqueous phase and functions to maintain the particle dispersed throughout the aqueous phase. The aqueous phase also comprises monomer (not shown). It will be appreciated that in practice the surface of the particle will have many steric stabilisers secured thereto, and that these have been omitted from the illustration in FIG. 1 for clarity.

Figure 2:
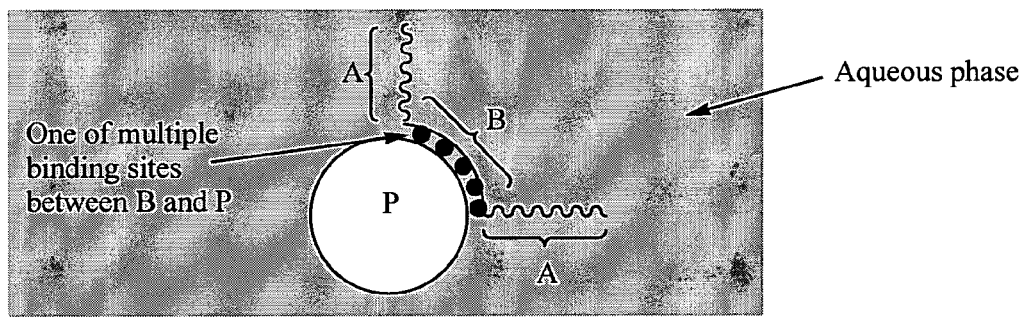
FIG. 2 presents a simplified schematic illustration not to scale showing: the multiple binding interactions between the anchoring polymeric segment (B) and the nanomagnetic particle (P), and the steric stabilising segments (A) solubilised in the aqueous phase. The aqueous phase also comprises monomer (not shown).

A similar illustration to that in FIG. 1 is shown in FIG. 2 where the steric stabiliser used in accordance with the invention is in the form of an A-B-A block copolymer.

As a block copolymer, the steric stabiliser used in accordance with the invention may be prepared by any suitable polymerisation technique. Having regard to the requirements of the polymeric segments A and B, those skilled in the art will be able to prepare suitable block copolymers using techniques well known in the art.

From FIGS. 1 and 2 and the discussion above, it will be appreciated that the polymer microgel beads in accordance with the invention comprise a polymeric matrix throughout which the nanomagnetic particles having steric stabiliser bound to the surface thereof are distributed in a substantially uniform manner. Despite being polymeric, it is to be noted that the steric stabiliser is a separate entity from and does not form part of the polymeric matrix of the beads. By "not forming part of the polymeric matrix of the beads" is meant that the steric stabiliser is not covalently bound to the crosslinked three dimensional network of polymer chains that form the polymeric matrix of the beads. Thus, when performing the method of the invention, the steric stabiliser does not take part in the polymerisation reaction of the one or more ethylenically unsaturated monomers that ultimately give rise to the polymeric matrix of the beads.

In one embodiment, the steric stabilising polymeric segment and/or the anchoring polymeric segment of the steric stabiliser used in accordance with the invention is prepared using a living polymerisation technique as herein described.

In a further embodiment, at least the anchoring polymeric segment of the steric stabiliser used in accordance with the invention is prepared using a living polymerisation technique as herein described. Of the living polymerisation techniques described herein, RAFT polymerisation is preferred.

RAFT polymerisation is a well described radical polymerisation technique that enables polymers to be prepared having a well defined molecular architecture and a low poly dispersity. RAFT polymerisation is conducted using a RAFT agent, and polymers formed under the control of the RAFT agent (i.e. polymerised via a RAFT mechanism to form polymer) may be conveniently referred to as a "RAFT polymer" or a "RAFT derived polymer".

In one embodiment of the invention, the steric stabiliser is a RAFT derived polymer.

Those skilled in the art will appreciate that RAFT agents are commonly depicted as having the general structure Z—C(S)—S—R, and that on formation a RAFT derived polymer will comprise the reaction residue of the RAFT agent. Under appropriate conditions, this reaction residue of the RAFT that forms part of the RAFT derived polymer may take part in subsequent polymerisation reactions. Thus, where a steric stabiliser used in accordance with the invention is a RAFT derived polymer, any potential for the polymer to take part in a polymerisation reaction with ethylenically unsaturated monomers will need to be deactivated. There are numerous techniques known in the art for modifying RAFT derived polymers such that the polymer is rendered incapable of taking part in a subsequent RAFT polymerisation reaction (e.g. the removal of the sulphur containing groups). For example, the RAFT derived polymer may be reacted with benzoyl peroxide.

Accordingly, in the event that a polymerisation technique used to prepare the steric stabiliser produces a polymer product having functional groups capable of taking part in a free radical polymerisation process, then these functional groups are to be deactivated toward free radical polymerisation so as to render the polymer suitable for use as a steric stabiliser in accordance with the invention.

With this in mind, a RAFT derived precursor to a steric stabiliser that may be used in accordance with the invention (hereinafter generically referred to as a "steric stabiliser precursor") might have a structure depicted by general formula (I):

where X represents alone or in conjunction with $R^1$ or Z the polymeric structure of the steric stabiliser (e.g. having a A-B or A-B-A block copolymer structure etc as hereinbefore described), $R^1$ and Z are groups derived from the RAFT agent used in preparing the steric stabiliser and are independently selected such that it can function as a RAFT agent in the polymerisation of the monomers that give rise to X.

Where $R^1$ or Z functions as part of the steric stabiliser, it will generally function as the steric stabilising polymeric segment, in which case X will represent the anchoring polymeric segment. In such an embodiment, $R^1$ or Z will present steric stabilising properties as herein described, and X will be an anchoring polymeric segment as herein described that has been formed by RAFT polymerisation.

In order to function as a RAFT agent in the polymerisation of the one or more ethylenically unsaturated monomers, those skilled in the art will appreciate that $R^1$ will typically be an organic group that functions as a free radical leaving group under the polymerisation conditions employed and yet, as a free radical leaving group, retains the ability to reinitiate polymerisation. Similarly, those skilled in the art will appreciate that Z will typically be an organic group that functions to give a suitably high reactivity of the C=S moiety in the RAFT agent towards free radical addition without slowing the rate of fragmentation of the RAFT-adduct radical to the extent that polymerisation is unduly retarded.

Examples of suitable $R^1$ groups include alkyl, alkylaryl, alkoxyaryl, alkoxyheteroaryl, and a polymer chain, each of which is optionally substituted with one or more hydrophilic groups.

More specific examples of suitable $R^1$ groups can include $C_1$-$C_6$ alkyl, $C_1$-$C_6$ alkyl aryl, $C_1$-$C_6$ alkoxy aryl or heteroaryl, and a polymer chain selected from polyalkylene oxide polymers such as water soluble polyethylene glycol or polypropylene glycol, and alkyl end capped derivatives thereof, each of which is optionally substituted with one or more hydrophilic groups selected from —$CO_2H$, —$CO_2RN$, —$SO_3H$, —$OSO_3H$, —SORN, —$SO_2RN$, —OP(OH)$_2$, —P(OH)$_2$, —PO(OH)$_2$, —OH, —ORN, —(OCH$_2$—CHR)$_w$—OH, —CONH$_2$, CONHR', CONR'R", —NR'R", —N$^+$R'R"R'", where R is selected from $C_1$-$C_6$ alkyl, w is 1 to 10, R', R" and R'" are independently selected from alkyl and aryl which are optionally substituted with one or more hydrophilic substituents selected from —$CO_2H$, —$SO_3H$, —$OSO_3H$, —OH, —(COCH$_2$CHR)$_w$—OH, —CONH$_2$, —SOR and $SO_2R$, and salts thereof, R and w are as defined above. Preferred $R^1$ groups include, but are not limited to, —CH(CH$_3$)CO$_2$H, —CH(CO$_2$H)CH$_2$CO$_2$H, —C(CH$_3$)$_2$CO$_2$H, —CH(CH$_3$)CO$_2$(CH$_2$CH$_2$O)$_n$H and —CH(CH$_3$)CO$_2$(CH$_2$CH$_2$O)$_n$CH$_3$, where n is ranges from about 5 to about 50, or from about 10 to about 25.

Suitable Z groups may be selected from optionally substituted alkoxy, optionally substituted aryloxy, optionally substituted alkyl, optionally substituted aryl, optionally substituted heterocyclyl, optionally substituted arylalkyl, optionally substituted alkylthio, optionally substituted aralkylthio, dialkoxy- or diaryloxy-phosphinyl [—P(=O)$R^2_2$], dialkyl- or diaryl-phosphinyl [—P(=O)$R^2_2$], optionally substituted acylamino, optionally substituted acylimino, optionally substituted amino, $R^1$—(X)—S— and a polymer chain, for example one selected from polyalkylene oxide polymers such as water soluble polyethylene glycol or polypropylene glycol, and alkyl end capped derivatives thereof, where $R^1$ and X are as defined above and $R^2$ is selected from optionally substituted $C_1$-$C_{18}$ alkyl, optionally substituted $C_2$-$C_{18}$ alkenyl, optionally substituted aryl, optionally substituted heterocyclyl, optionally substituted aralkyl, and optionally substituted alkaryl.

Preferred Z groups include, but are not limited to, —CH$_2$(C$_6$H$_5$), $C_1$-$C_{20}$ alkyl,

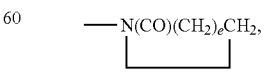

where e is 2 to 4, and —SR$^3$, where R$^3$ is selected from $C_1$ to $C_{20}$ alkyl.

Preferred optional substituents for $R^2$ and Z groups include epoxy, hydroxy, alkoxy, acyl, acyloxy, carboxy (and salts), sulfonic acid (and salts), alkoxy- or aryloxy-carbonyl, isocyanato, cyano, silyl, halo, and dialkylamino.

In selecting both $R^1$ and Z groups of formula (I), all combinations of preferred $R^1$ and Z groups are also preferred.

Where the hydrophilic group is —N+R'R"R'" there will be an associated counter anion.

$R^1$ may also be an organic group optionally substituted with one or more hydrophobic groups. In that case, Z is preferably an organic group optionally substituted with one or more hydrophilic groups.

As used herein, the terms "aryl" and "heteroaryl" refer to any substituent which includes or consists of one or more aromatic or heteroaromatic ring respectively, and which is attached via a ring atom. The rings may be mono or polycyclic ring systems, although mono or bicyclic 5 or 6 membered rings are preferred. Examples of suitable rings include but are not limited to benzene, biphenyl, terphenyl, quaterphenyl, naphthalene, tetrahydronaphthalene, 1-benzylnaphthalene, anthracene, dihydroanthracene, benzanthracene, dibenzanthracene, phenanthracene, perylene, pyridine, 4-phenylpyridine, 3-phenylpyridine, thiophene, benzothiophene, naphthothiophene, thianthiene, furan, benzofuran, pyrene, isobenzofuran, chromene, xanthene, phenoxathiin, pyrrole, imidazole, pyrazole, pyrazine, pyrimidine, pyridazine, indole, indolizine, isoindole, purine, quinoline, isoquinoline, phthalazine, quinoxaline, quinazoline, pteridine, carbazole, carboline, phenanthridine, acridine, phenanthroline, phenazine, isothiazole, isooxazole, phenoxazine and the like, each of which may be optionally substituted.

In this specification "optionally substituted" means that a group may or may not be further substituted with one or more groups selected from, but not limited to, alkyl, alkenyl, alkynyl, aryl, halo, haloalkyl, haloalkenyl, haloalkynyl, haloaryl, hydroxy, alkoxy, alkenyloxy, aryloxy, benzyloxy, haloalkoxy, haloalkenyloxy, acetyleno, carboximidyl, haloaryloxy, isocyano, cyano, formyl, carboxyl, nitro, nitroalkyl, nitroalkenyl, nitroalkynyl, nitroaryl, alkylamino, dialkylamino, alkenylamino, alkynylamino, arylamino, diarylamino, benzylamino, imino, alkylimine, alkenylimine, alkynylimino, arylimino, benzylimino, dibenzylamino, acyl, alkenylacyl, alkynylacyl, arylacyl, acylamino, diacylamino, acyloxy, alkylsulphonyloxy, arylsulphenyloxy, heterocyclyl, heterocycloxy, heterocyclamino, haloheterocyclyl, alkylsulphonyl, arylsulphonyl, alkylsolphinyl, arylsulphinyl, carboalkoxy, alkylthio, benzylthio, acylthio, sulphonamido, sulfanyl, sulfo and phosphorus-containing groups, alkoxysilyl, silyl, alkylsilyl, alkylalkoxysilyl, phenoxysilyl, alkylphenoxysilyl, alkoxyphenoxysilyl, arylphenoxysilyl, allophanyl, guanidino, hydantoyl, ureido, and ureylene.

Unless stated otherwise, the terms "halogen" and "halo" used herein refer to I, Br, Cl and F.

In this specification the term "alkyl", used either alone or in compound words such as "alkenyloxyalkyl", "alkylthio", "alkylamino" and "dialkylamino" denotes straight chain, branched or cyclic alkyl, preferably $C_{1-20}$ alkyl or cycloalkyl. Examples of straight chain and branched alkyl include methyl, ethyl, propyl, isopropyl, butyl, isobutyl, sec-butyl, tert-butyl, amyl, isoamyl, sec-amyl, 1,2-dimethylpropyl, 1,1-dimethyl-propyl, hexyl, 4-methylpentyl, 1-methylpentyl, 2-methylpentyl, 3-methylpentyl, 1,1-dimethylbutyl, 2,2-dimethylbutyl, 3,3-dimethylbutyl, 1,2-dimethylbutyl, 1,3-dimethylbutyl, 1,2,2,-trimethylpropyl, 1,1,2-trimethylpropyl, heptyl, 5-methoxyhexyl, 1-methylhexyl, 2,2-dimethylpentyl, 3,3-dimethylpentyl, 4,4-dimethylpentyl, 1,2-dimethylpentyl, 1,3-dimethylpentyl, 1,4-dimethyl-pentyl, 1,2,3,-trimethylbutyl, 1,1,2-trimethylbutyl, 1,1,3-trimethylbutyl, octyl, 6-methylheptyl, 1-methylheptyl, 1,1,3,3-tetramethylbutyl, nonyl, 1-, 2-, 3-, 4-, 5-, 6- or 7-methyl-octyl, 1-, 2-, 3-, 4- or 5-ethylheptyl, 1-, 2- or 3-propylhexyl, decyl, 1-, 2-, 3-, 4-, 5-, 6-, 7- and 8-methylnonyl, 1-, 2-, 3-, 4-, 5- or 6-ethyloctyl, 1-, 2-, 3- or 4-propylheptyl, undecyl, 1-, 2-, 3-, 4-, 5-, 6-, 7-, 8- or 9-methyldecyl, 1-, 2-, 3-, 4-, 5-, 6- or 7-ethylnonyl, 1-, 2-, 3-, 4- or 5-propyloctyl, 1-, 2- or 3-butylheptyl, 1-pentylhexyl, dodecyl, 1-, 2-, 3-, 4-, 5-, 6-, 7-, 8-, 9- or 10-methylundecyl, 1-, 2-, 3-, 4-, 5-, 6-, 7- or 8-ethyldecyl, 1-, 2-, 3-, 4-, 5- or 6-propylnonyl, 1-, 2-, 3- or 4-butyloctyl, 1-2-pentylheptyl and the like. Examples of cyclic alkyl include mono- or polycyclic alkyl groups such as cyclopropyl, cyclobutyl, cyclopentyl, cyclohexyl, cycloheptyl, cyclooctyl, cyclononyl, cyclodecyl and the like.

As used herein, the term "salt" denotes a species in ionised form, and includes both acid addition and base addition salts. In the context of forming a RAFT polymer, suitable salts are those that do not interfere with the RAFT chemistry.

As used herein, the term "counter anion" denotes a species capable of providing a negative charge to balance the charge of the corresponding cation. Examples of counter anions include, $Cl^-$, $I^-$, $Br^-$, $F^-$, $NO_3^-$, $CN^-$ and $PO_3^-$.

As used herein, the term "alkoxy" denotes straight chain or branched alkoxy, preferably $C_{1-20}$ alkoxy. Examples of alkoxy include methoxy, ethoxy, n-propoxy, isopropoxy and the different butoxy isomers.

As used herein, the term "alkenyl" denotes groups formed from straight chain, branched or cyclic alkenes including ethylenically mono-, di- or poly-unsaturated alkyl or cycloalkyl groups as previously defined, preferably $C_{2-20}$ alkenyl. Examples of alkenyl include vinyl, allyl, 1-methylvinyl, butenyl, iso-butenyl, 3-methyl-2-butenyl, 1-pentenyl, cyclopentenyl, 1-methyl-cyclopentenyl, 1-hexenyl, 3-hexenyl, cyclohexenyl, 1-heptenyl, 3-heptenyl, 1-octenyl, cyclooctenyl, 1-nonenyl, 2-nonenyl, 3-nonenyl, 1-decenyl, 3-decenyl, 1,3-butadienyl, 1-4,pentadienyl, 1,3-cyclopentadienyl, 1,3-hexadienyl, 1,4-hexadienyl, 1,3-cyclohexadienyl, 1,4-cyclohexadienyl, 1,3-cycloheptadienyl, 1,3,5-cycloheptatrienyl and 1,3,5,7-cyclooctatetraenyl.

As used herein, the term "alkynyl" denotes groups formed from straight chain, branched or cyclic alkyne including those structurally similar to the alkyl and cycloalkyl groups as previously defined, preferably $C_{2-20}$ alkynyl. Examples of alkynyl include ethynyl, 2-propynyl and 2- or 3-butynyl.

As used herein, the term "acyl" either alone or in compound words such as "acyloxy", "acylthio", "acylamino" or "diacylamino" denotes carbamoyl, aliphatic acyl group and acyl group containing an aromatic ring, which is referred to as aromatic acyl or a heterocyclic ring which is referred to as heterocyclic acyl, preferably $C_{1-20}$ acyl. Examples of acyl include carbamoyl; straight chain or branched alkanoyl such as formyl, acetyl, propanoyl, butanoyl, 2-methylpropanoyl, pentanoyl, 2,2-dimethylpropanoyl, hexanoyl, heptanoyl, octanoyl, nonanoyl, decanoyl, undecanoyl, dodecanoyl, tridecanoyl, tetradecanoyl, pentadecanoyl, hexadecanoyl, heptadecanoyl, octadecanoyl, nonadecanoyl and icosanoyl; alkoxycarbonyl such as methoxycarbonyl, ethoxycarbonyl, t-butoxycarbonyl, t-pentyloxycarbonyl and heptyloxycarbonyl; cycloalkylcarbonyl such as cyclopropylcarbonyl, cyclobutylcarbonyl, cyclopentylcarbonyl and cyclohexylcarbonyl; alkylsulfonyl such as methylsulfonyl and ethylsulfonyl; alkoxysulfonyl such as methoxysulfonyl and ethoxysulfonyl; aroyl such as benzoyl, toluoyl and naphthoyl; aralkanoyl such as phenylalkanoyl (e.g. phenylacetyl, phenylpropanoyl, phenylbutanoyl, phenylisobutylyl, phenylpentanoyl and phenylhexanoyl) and naphthylalkanoyl (e.g. naphthylacetyl, naphthylpropanoyl and naphthylbutanoyl; aralkenoyl such as phenylalkenoyl (e.g. phenylpropenoyl, phenylbutenoyl, phenylmethacryloyl, phenylpentenoyl and phenylhexenoyl and naphthylalkenoyl (e.g. naphthylpropenoyl, naphthylbutenoyl and naphthylpentenoyl); aralkoxycarbonyl such as phenylalkoxycarbonyl (e.g. benzyloxycarbonyl); aryloxycarbonyl such as phenoxycarbonyl and napthyloxycarbonyl; aryloxyalkanoyl such as phenoxyacetyl and phenoxypropionyl; arylcarbamoyl such as phenylcarbamoyl; arylthiocarbamoyl such as phenylthiocarbamoyl; arylglyoxyloyl such as phenylglyoxyloyl and naphthylglyoxyloyl; arylsulfonyl such as phenylsulfonyl and napthylsulfonyl; heterocycliccarbonyl; heterocyclicalkanoyl such as thienylacetyl, thienylpropanoyl, thienylbutanoyl, thienylpentanoyl, thienylhexanoyl, thiazolylacetyl, thiadiazolylacetyl and tetrazolylacetyl; heterocyclicalkenoyl such as heterocyclicpropenoyl, heterocyclicbutenoyl, heterocyclicpentenoyl and heterocyclichexenoyl; and heterocyclicglyoxyloyl such as thiazolylglyoxyloyl and thienylglyoxyloyl.

As used herein, the terms "heterocyclic", "heterocyclyl" and "heterocycle" used on their own or as part of a term such as "heterocyclicalkenoyl", heterocycloxy" or "haloheterocyclyl" refer to aromatic, pseudo-aromatic and non-aromatic rings or ring systems which contain one or more heteroatoms selected from N, S, and O and which may be optionally substituted. Preferably the rings or ring systems have 3 to 20 carbon atoms. The rings or ring systems may be selected from those described above in relation to the definition of "heteroaryl".

Preferred steric stabiliser precursors of formula (I) include, but are not limited to, the following general formulas (II) to (X):

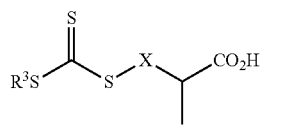
(II)

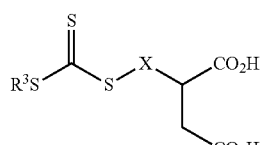
(III)

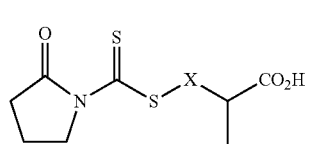
(IV)

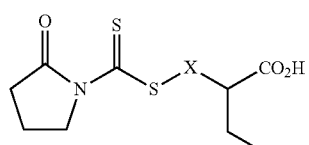
(V)

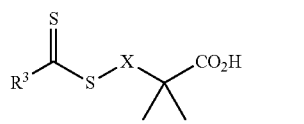
(VI)

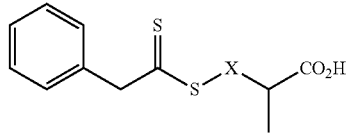
(VII)

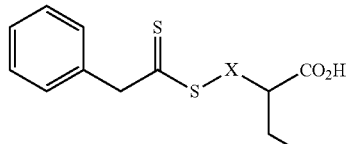
(VIII)

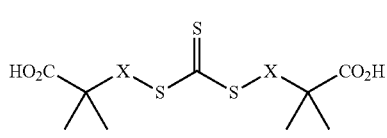
(IX)

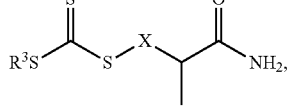
(X)

structures (II) to (IX) wherein one or both —$CO_2H$ group(s) in each structure is replaced by —$CH(CH_3)CO_2(CH_2CH_2O)_n$H or —$CH(CH_3)CO_2(CH_2CH_2O)_nCH_3$, structures (II), (III), (VI) and (X) wherein $R^3$ is replaced by —CH$(CH_3)CO_2(CH_2CH_2O)_n$H or —$CH(CH_3)CO_2(CH_2CH_2O)_n$CH_3$, structures (VII) and (VIII) wherein PhCH_2— is replaced by —$CH(CH_3)CO_2(CH_2CH_2O)_n$H or —$CH(CH_3)CO_2(CH_2CH_2O)_nCH_3$, and structures (IV) and (V) wherein the 5-membered nitrogen heterocycle is replaced by —CH$(CH_3)CO_2(CH_2CH_2O)_n$H or —$CH(CH_3)CO_2(CH_2CH_2O)_nCH_3$, where n is ranges from about 5 to about 50, or from about 10 to about 25, where $R^3$ and X are as previously defined.

Preparing a steric stabiliser precursor by RAFT polymerisation may involve polymerising under the control of a RAFT agent (i) one or more type of ethylenically unsaturated monomer to provide for at least one steric stabilising polymeric segment (A), and (ii) one or more type of different monomers to provide for at least one anchoring polymeric segment (B) (i.e. where A and B collectively form X in structure (I)). Alternatively, a steric stabiliser precursor prepared by RAFT polymerisation may involve polymerising under the control of a RAFT agent (i) one or more type of ethylenically unsaturated monomer to provide for at least one steric stabilising polymeric segment (A), or (ii) one or more type of different monomers to provide for at least one anchoring polymeric segment (B) (i.e. where only one of A and B form X in structure (I) and $R^1$ in effect represents the other). Techniques, conditions and reagents known by those skilled in the art of RAFT polymerisation may be conveniently used to prepare such stabilisers precursors.

Suitable RAFT agents for preparing such steric stabiliser precursors include, but are not limited to, those of general formula (IA):

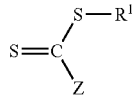
(IA)

where $R^1$ and Z are as previously defined.

In selecting both $R^1$ and Z groups for RAFT agents of the formula (IA), those agents resulting from the combination of preferred $R^1$ and Z groups are also preferred Preferred RAFT agents for preparing a steric stabiliser precursor include, but are not limited to, those represented by the following general formulas (XI) to (IXX):

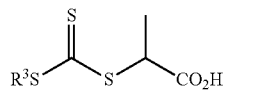
(XI)

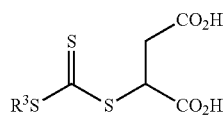
(XII)

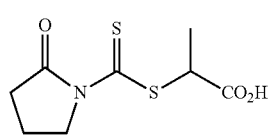
(XIII)

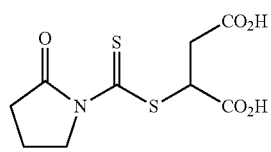
(XIV)

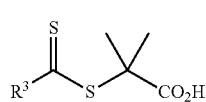
(XV)

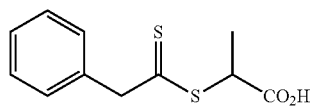
(XVI)

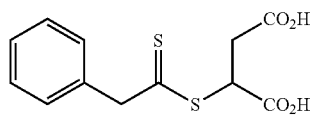
(XVII)

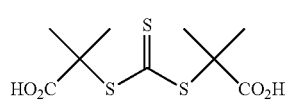
(XVIII)

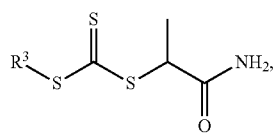
(IXX)

structures (XI) to (XVIII) wherein one or both —$CO_2H$ group(s) in each structure is replaced by —$CH(CH_3)CO_2(CH_2CH_2O)_nH$ or —$CH(CH_3)CO_2(CH_2CH_2O)_nCH_3$, structures (XI), (XII), (XV) and (IXX) wherein $R^3$ is replaced by —$CH(CH_3)CO_2(CH_2CH_2O)_nH$ or —$CH(CH_3)CO_2(CH_2CH_2O)_nCH_3$, structures (XVI) and (XVII) wherein $PhCH_2$— is replaced by —$CH(CH_3)CO_2(CH_2CH_2O)_nH$ or —$CH(CH_3)CO_2(CH_2CH_2O)_nCH_3$, and structures (XIII) and (XIV) wherein the 5-membered nitrogen heterocycle is replaced by —$CH(CH_3)CO_2(CH_2CH_2O)_nH$ or —$CH(CH_3)CO_2(CH_2CH_2O)_nCH_3$, where n is ranges from about 5 to about 50, or from about 10 to about 25, where $R^3$ and X are as previously defined.

When preparing a block copolymer structure of the steric stabiliser by any polymerisation technique, including RAFT polymerisation, those skilled in the art will also appreciate that each segment can be formed sequentially by the polymerisation of appropriate monomers. Alternatively, a preformed polymer may be employed as one of the segments and the other segment may be grafted thereto by the polymerisation of appropriate monomers.

Having regard to the discussion above concerning the required attributes of monomers that may be used to prepare the polymeric matrix of the beads and the steric stabilising and anchoring polymeric segments, suitable monomers that may be used in general are those which can be polymerised by a free radical process. Suitable monomers should also be capable of being polymerised with other monomers. The factors which determine copolymerisability of various monomers are well documented in the art. For example, see: Greenlee, R. Z., in Polymer Handbook 3$^{rd}$ Edition (Brandup, J., and Immergut. E. H. Eds) Wiley: New York, 1989 p 11/53.

Such monomers, including those mentioned above, may be selected from those with the general formula (XX):

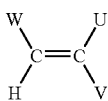
(XX)

where U and W are independently selected from the group consisting of —$CO_2H$, —$CO_2R^1$, —$COR^1$, —$CSR^1$, —$CSOR^1$, —$COSR^1$, —$CONH_2$, —$CONHR^1$, —$CONR^1_2$, hydrogen, halogen and optionally substituted $C_1$-$C_4$ alkyl, or U and W form together a lactone, anhydride or imide ring that may itself be optionally substituted, wherein the substituents are independently selected from the group consisting of hydroxy, —$CO_2H$, —$CO_2R^1$, —$COR^1$, —$CSR^1$, —$CSOR^1$, —$COSR^1$, —CN, —$CONH_2$, —$CONHR^1$, —$CONR^1_2$, —$OR^1$, —$SR^1$, —$O_2CR^1$, —$SCOR^1$, and —$OCSR^1$; and V is selected from the group consisting of hydrogen, $R^2$, —$CO_2H$, —$CO_2R^2$, —$COR^2$, —$CSOR^2$, —$COSR^2$, —$CONH_2$, —$CONHR^2$, —$CONR^2_2$, —$OR^2$, —$SR^2$, —$O_2CR^2$, —$SCOR^2$, and —$OCSR^2$;

where $R^2$ is selected from the group consisting of optionally substituted $C_1$-$C_{18}$ alkyl, optionally substituted $C_2$-$C_{18}$ alkenyl, optionally substituted aryl, optionally substituted heteroaryl, optionally substituted carbocyclyl, optionally substituted heterocyclyl, optionally substituted aralkyl, optionally substituted heteroarylalkyl, optionally substituted alkaryl, optionally substituted alkylheteroaryl and polymer chains wherein the substituents are independently selected from the group consisting of alkyleneoxidyl (epoxy), hydroxy, alkoxy, acyl, acyloxy, formyl, alkylcarbonyl, carboxy, sulfonic acid, alkoxy- or aryloxy-carbonyl, isocyanato, cyano, silyl, halo, amino, including salts and derivatives thereof. Preferred polymer chains include, but are not limited to, polyalkylene oxide, polyarylene ether and polyalkylene ether.

Examples of monomers of general formula (XX) include, but are not limited to, maleic anhydride, N-alkylmaleimide, N-arylmaleimide, dialkyl fumarate and cyclopolymerisable monomers, acrylate and methacrylate esters, acrylic and methacrylic acid, styrene, acrylamide, methacrylamide, and methacrylonitrile, mixtures of these monomers, and mixtures of these monomers with other monomers.

Further examples of monomers of general formula (XX) include the following:

methyl methacrylate, ethyl methacrylate, propyl methacrylate (all isomers), butyl methacrylate (all isomers), 2-ethylhexyl methacrylate, isobornyl methacrylate, methacrylic acid, benzyl methacrylate, phenyl methacrylate, methacrylonitrile, alpha-methylstyrene, methyl acrylate, ethyl acrylate, propyl acrylate (all isomers), butyl acrylate (all isomers), 2-ethylhexyl acrylate, isobornyl acrylate, acrylic acid, benzyl acrylate, phenyl acrylate, acrylonitrile, styrene, functional methacrylates, acrylates and styrenes selected from glycidyl methacrylate, 2-hydroxyethyl methacrylate, hydroxypropyl methacrylate (all isomers), hydroxybutyl methacrylate (all isomers), N,N-dimethylaminoethyl methacrylate, N,N-diethylaminoethyl methacrylate, triethyleneglycol methacrylate, itaconic anhydride, itaconic acid, glycidyl acrylate, 2-hydroxyethyl acrylate, hydroxypropyl acrylate (all isomers), hydroxybutyl acrylate (all isomers), N,N-dimethylaminoethyl acrylate, N,N-diethylaminoethyl acrylate, triethyleneglycol acrylate, methacrylamide, N-methylacrylamide, N,N-dimethylacrylamide, N-tert-butylmethacrylamide, N-n-butylmethacrylamide, N-methylolmethacrylamide, N-ethylolmethacrylamide, N-tert-butylacrylamide, N-n-butylacrylamide, N-methylolacrylamide, N-ethylolacrylamide, vinyl benzoic acid (all isomers), diethylamino styrene (all isomers), alpha-methylvinyl benzoic acid (all isomers), diethylamino alpha-methylstyrene (all isomers), p-vinylbenzene sulfonic acid, p-vinylbenzene sulfonic sodium salt, trimethoxysilylpropyl methacrylate, triethoxysilylpropyl methacrylate, tributoxysilylpropyl methacrylate, dimethoxymethylsilylpropyl methacrylate, diethoxymethylsilylpropyl methacrylate, dibutoxymethylsilylpropyl methacrylate, diisopropoxymethylsilylpropyl methacrylate, dimethoxysilylpropyl methacrylate, diethoxysilylpropyl methacrylate, dibutoxysilylpropyl methacrylate, diisopropoxysilylpropyl methacrylate, trimethoxysilylpropyl acrylate, triethoxysilylpropyl acrylate, tributoxysilylpropylacrylate, dimethoxymethylsilylpropyl acrylate, diethoxymethylsilylpropyl acrylate, dibutoxymethylsilylpropyl acrylate, diisopropoxymethylsilylpropyl acrylate, dimethoxysilylpropyl acrylate, diethoxysilylpropyl acrylate, dibutoxysilylpropyl acrylate, diisopropoxysilylpropyl acrylate, vinyl acetate, vinyl butyrate, vinyl benzoate, vinyl chloride, vinyl fluoride, vinyl bromide, maleic anhydride, N-phenylmaleimide, N-butylmaleimide, N-vinylpyrrolidone, N-vinylcarbazole, butadiene, ethylene and chloroprene. This list is not exhaustive.

When performing the method of the invention, or selecting or preparing a steric stabiliser for use in accordance with the invention, in addition to selecting the stabiliser or suitable ethylenically unsaturated monomers having regard to the requirements outlined above, the stabiliser and/or monomers may also be selected to present polymers having desired properties in the context of the intended application for the polymer microgel beads. For example, the stabiliser and/or monomers may be selected so as to present polymers that are biodegradable and/or biocompatible.

Upon providing the dispersion as herein described, the one or more ethylenically unsaturated monomers present in the aqueous phase are polymerised to thereby form the polymer microgel beads incorporating the nanomagnetic particles. The polymerisation process may be conducted using conditions, reagents and equipment well known to those skilled in the art. Generally, the polymerisation will be performed in batch mode using conventional mini-emulsion or suspension polymerisation techniques.

When preparing the microgel beads of the invention, or preparing a steric stabiliser for use in accordance with the invention by the polymerisation of ethylenically unsaturated monomers, the polymerisation may require initiation from a source of free radicals. The source of initiating radicals can be provided by any suitable method of generating free radicals, such as the thermally induced homolytic scission of suitable compound(s) (thermal initiators such as peroxides, peroxyesters, or azo compounds), the spontaneous generation from monomers (e.g. styrene), redox initiating systems, photochemical initiating systems or high energy radiation such as electron beam, X- or gamma-radiation. The initiating system is chosen such that under the reaction conditions there is no substantial adverse interaction between the initiator or the initiating radicals and other reagents present.

The type and amount of initiators that may be used in the method of the invention will generally be substantially soluble in the aqueous phase at the temperature at which the polymerisation is conducted.

Thermal initiators are chosen to have an appropriate half life at the temperature of polymerisation. These initiators can include one or more of the following compounds:

2,2'-azobis(isobutyronitrile), 2,2'-azobis(2-cyanobutane), dimethyl 2,2'-azobis(isobutyrate), 4,4'-azobis(4-cyanovaleric acid), 1,1'-azobis(cyclohexanecarbonitrile), 2-(t-butylazo)-2-cyanopropane, 2,2'-azobis{2-methyl-N-[1,1-bis(hydroxymethyl)-2-hydroxyethyl]propionamide}, 2,2'-azobis[2-methyl-N-(2-hydroxyethyl)propionamide], 2,2'-azobis(N,N'-dimethyleneisobutyramidine) dihydrochloride, 2,2'-azobis(2-amidinopropane) dihydrochloride, 2,2'-azobis (N,N'-dimethyleneisobutyramidine), 2,2'-azobis{2-methyl-N-[1,1-bis(hydroxymethyl)-2-hydroxyethyl] propionamide}, 2,2'-azobis{2-methyl-N-[1,1-bis (hydroxymethyl)-2-ethyl]propionamide}, 2,2'-azobis [2-methyl-N-(2-hydroxyethyl)propionamide], 2,2'-azobis(isobutyramide) dihydrate, 2,2'-azobis(2,2,4-trimethylpentane), 2,2'-azobis(2-methylpropane), t-butyl peroxyacetate, t-butyl peroxybenzoate, t-butyl peroxyneodecanoate, t-butylperoxy isobutyrate, t-amyl peroxypivalate, t-butyl peroxypivalate, diisopropyl peroxydicarbonate, dicyclohexyl peroxydicarbonate, dicumyl peroxide, dibenzoyl peroxide, dilauroyl peroxide, potassium peroxydisulfate, ammonium peroxydisulfate, di-t-butyl hyponitrite, dicumyl hyponitrite. This list is not exhaustive.

Photochemical initiator systems are chosen to have the requisite solubility in the reaction medium and have an appropriate quantum yield for radical production under the conditions of the polymerisation. Examples include benzoin derivatives, benzophenone, acyl phosphine oxides, and photo-redox systems.

Redox initiator systems are chosen to have the requisite solubility in the reaction medium and have an appropriate rate of radical production under the conditions of the polymerisation; these initiating systems can include, but are not limited to, combinations of the following oxidants and reductants:

oxidants: potassium, peroxydisulfate, hydrogen peroxide, t-butyl hydroperoxide.

reductants: iron (II), titanium (III), potassium thiosulfite, potassium bisulfite.

Other suitable initiating systems are described in recent texts. See, for example, Moad and Solomon "the Chemistry of Free Radical Polymerisation", Pergamon, London, 1995, pp 53-95.

Suitable initiators which have an appreciable solubility in a hydrophilic reaction medium such as water include, but are not limited to, 4,4-azobis(cyanovaleric acid), 2,2'-azobis{2-methyl-N-[1,1-bis(hydroxymethyl)-2-hydroxyethyl]propionamide}, 2,2'-azobis[2-methyl-N-(2-hydroxyethyl)propionamide], 2,2'-azobis(N,N'-dimethyleneisobutyramidine), 2,2'-azobis(N,N-dimethyleneisobutyramidine) dihydrochloride, 2,2'-azobis(2-amidinopropane) dihydrochloride, 2,2'-azobis{2-methyl-N-[1,1-bis(hydroxymethyl)-2-ethyl]propionamide}, 2,2'-azobis[2-methyl-N-(2-hydroxyethyl) propionamide], 2,2'-azobis(isobutyramide) dihydrate, and derivatives thereof.

Suitable initiators which have an appreciable solubility in a hydrophobic reaction medium may vary depending on the polarity of the reaction medium, but typically would include oil soluble initiators such as azo compounds exemplified by the well known material 2,2'-azobisisobutyronitrile. Other readily available initiators are acyl peroxides such as acetyl and benzoyl peroxide as well as alkyl peroxides such as cumyl and t-butyl peroxides. Hydroperoxides such as t-butyl and cumyl hydroperoxides may also be used.

One approach for preparing the microgel beads of the invention using a bulk polymerisation technique might involve first preparing the nanomagnetic particles (optionally together with a radioactive isotope) in an aqueous solution and then adding to this solution an appropriate steric stabiliser, ethylenically unsaturated monomer that is soluble in the aqueous medium and a thermal initiator. The resulting aqueous solution may then be combined with an organic medium comprising a dispersing agent, and the resulting combination agitated so as to form the dispersion used in accordance with the invention. Typically, all reagents used are essentially free from dissolved oxygen and the dispersion is purged with an inert gas, such as nitrogen, prior to initiating polymerisation. Having prepared the dispersion, its temperature may be increased so that the initiator undergoes thermally induced homolytic scission and promotes polymerisation of the one or more ethylenically unsaturated monomers present in the aqueous phase. Polymerisation of the monomers results in formation of the polymer microgel beads incorporating the nanomagnetic particles, and the beads may be isolated for subsequent use.

The polymer microgel beads in accordance with the invention may be used in various applications. It is believed that the beads are particularly suited for use in biomedical applications such as inducing hyperthermia in tissue. Hyperthermia has been proposed as a treatment of diseased tissue. There is evidence to suggest that hyperthermia is effective in treating diseases, including cancerous growths. The therapeutic benefit of hyperthermia therapy is believed to be mediated through two principle mechanisms. Firstly, hyperthermia therapy has a direct tumouricidal effect on tissue by raising temperatures to greater than about 41 or 42° C. resulting in irreversible damage to cancer cells. Secondly, hyperthermia is known to sensitise cancer cells to the effects of radiation therapy and to certain chemotherapeutic drugs.

In contrast to radiotherapy or chemotherapy, hyperthermia therapy is not prone to any cumulative toxicity effects.

The present invention therefore also provides a composition suitable for administration to a subject, the composition comprising polymer microgel beads in accordance with the invention and a pharmacologically acceptable carrier.

Compositions in accordance with the invention are suitable for administration to a subject. By the term "subject" is meant either an animal or human subject. By "animal" is meant primates, livestock animals (including cows, horses, sheep, pigs and goats), companion animals (including dogs, cats, rabbits and guinea pigs), and captive wild animals (including those commonly found in a zoo environment). Laboratory animals such as rabbits, mice, rats, guinea pigs and hamsters are also contemplated as they may provide a convenient test system. Preferably, the subject is a human subject.

By the composition being "suitable" for administration to a subject is meant that administration of the composition to a subject will not result in unacceptable toxicity, including allergenic responses and disease states.

By "administration" of the composition to a subject is meant that the composition is transferred to the subject. There is no particular limitation on the mode of administration, and the intended application will generally dictate the mode of administration. Generally, the compositions are administered in such a way as to cause the polymer microgel beads to concentrate in a target site. For example, the composition may be administered via intratumoral, peritumoral, or intravascular, intravenous, intraperitoneal, subcutaneous, intrahecal injection or superficial applications. The compositions in accordance with the invention are preferably administered via the arterial or venous blood supply.

The compositions in accordance with the invention comprise a pharmacologically acceptable carrier. By "pharmacologically acceptable" is meant that the carrier is suitable for administration to a subject in its own right. In other words, administration of the carrier to a subject will not result in unacceptable toxicity, including allergenic responses and disease states. The term "carrier" refers to the vehicle with which the polymer microgel beads are contained prior to being administered.

As a guide only, a person skilled in the art may consider "pharmacologically acceptable" as an entity approved by a regulatory agency of a federal or state government or listed in the US Pharmacopeia or other generally recognised pharmacopeia for use in animals, and more particularly humans.

Suitable pharmacologically acceptable carriers are described in Martin, Remington's Pharmaceutical Sciences, 18$^{th}$ Ed., Mack Publishing Co., Easton, Pa., (1990), and include, but are not limited to, liquids that may be sterilised such as water and oils, including those of petroleum, animal, vegetable or synthetic origin, such as peanut oil, soya bean oil, mineral oil, sesame oil, and the like. Water or soluble saline solutions and aqueous dextrose and glycerol solutions are preferably employed as carriers, particularly for injectable solutions.

The compositions in accordance with the invention may also include diluents of various buffer content (e.g. Tris-HCL, acetate, phosphate), pH and ionic strength; additives such as solubilising agents, anti-oxidants, and preservatives.

The compositions in accordance with the invention may be used to provide hyperthermic treatment of a target site of interest in a subject.

As used herein, a "target site of interest in a subject" is intended to mean a region of the subject that is considered to warrant hyperthermic treatment. There is no particular limitation regarding the location of the target site provided that the composition in accordance with the invention can be administered to it and that the target site can be exposed to the appropriate magnetic field. The target site will generally be diseased tissue, such as cancerous tissue.

A preferred use of compositions in accordance with the invention is to provide hyperthermic treatment of deep seated cancers such as liver cancer.

When used to heat subject tissue, the compositions in accordance with the invention preferably comprise polymer microgel beads of a size which ensures they are capable of being trapped in the capillary bed of the tissue (e.g. tumour) rather than being able to pass through the tissue into the venous supply. To effect this entrapment, the beads will preferably have a size ranging from about 10 microns to about 100 microns.

In order to promote the hyperthermic treatment, the target site is exposed to a magnetic field of clinically acceptable frequency and strength that causes the beads to radiate heat at the target site. By a magnetic field of a "clinically acceptable frequency and strength" is meant a magnetic field that will not result in unacceptable or undesirable physiological response in the subject being treated, be it from the magnetic field per se or its effect on the beads to radiate heat.

Generally, the magnetic field employed will be an alternating or AC magnetic field.

Upon being exposed to the magnetic field, the polymer microgel beads at the target site will generally exhibit a VAR of at least about 1 Watts/cm$^3$, more preferably at least about 10 Watts/cm$^3$, most preferably at least about 20 Watts/cm$^3$.

Generally, the beads at the target site will be exposed to an AC magnetic field with frequency in the range of about 50-300 kHz and strength of about 50-120 Oe, for example at a frequency of about 100 kHz and a strength of about 90 Oe.

Exposure of the target site to the appropriate magnetic field causes the polymer microgel beads at the site to heat, and this heat is conducted into the immediately surrounding site (e.g. diseased tissue). This method of heat treatment is generally known as Selectively Targeted Hyperthermia (STH).

It will be appreciated that adequate heating of the target site will be required for the hyperthermic treatment to be effective. Thus, the method for heating a target site in accordance with the invention provides a means to increase temperature in the target site to above 41° C. For use on the treatment of diseased tissue, the desired result is to decrease the viability of malignant cells. A decrease in the viability of malignant cells can result in either cell death or increased cell sensitivity to the effects of ionising radiation or chemotherapeutic drugs.

It is preferable that the method of heating a target site in accordance with the invention promotes heating of 42° C. at the target site for at least 30 minutes. The level of heating induced by the implanted polymer microgel beads will depend on several factors, including the VAR of the beads, the amount of material that can be localised in and around the target site, and the cooling factors in the environment of the polymer beads, such as blood perfusion.

The microgel beads may be administered in, as appropriate, a treatment or diagnostic effective amount. A treatment or diagnostic effective amount is intended to include an amount which, when administered according to the desired dosing regimen, achieves a desired therapeutic or diagnostic effect, including one or more of: alleviating the symptoms of, preventing or delaying the onset of, inhibiting or slowing the progression of, diagnosing, or halting or reversing altogether the onset or progression of a particular condition being treated and/or assessed.

Suitable dosage amounts and dosing regimens to achieve this can be determined by the attending physician and may depend on the particular condition being treated or diagnosed, the severity of the condition as well the general age, health and weight of the subject.

Compositions comprising the microgel beads may be administered in a single dose or a series of doses.

Where the compositions comprising the microgel beads are suitable for parenteral administration, they will generally be in the form of an aqueous or non-aqueous isotonic sterile injection solution that may contain one or more of an anti-oxidant, buffer, bactericide or solute which renders the composition isotonic with the blood of the intended subject. Such compositions may be presented in unit-dose or multi-dose sealed containers, for example, ampoules and vials.

In some applications it may be desirable to image the polymer microgel beads once they have been administered to a subject. The beads may therefore comprise a radioactive isotope for imaging purposes. Examples of suitable radioactive isotopes include $^{99m}$Tc, $^{67}$Ga, $^{64}$Cu, $^{89}$Zr and $^{18}$F. The beads may be radioactively labeled by any suitable means. For example, the isotope(s) may be conveniently combined with the nanomagnetic particles used in accordance with the invention.

The invention will now be described with reference to the following examples which illustrate some preferred embodiments of the invention. However, it is to be understood that the particularity of the following description is not to supersede the generality of the proceeding description of the invention.

EXAMPLES

Example 1

Preparation of a poly(acrylamide) Microgel Matrix Incorporating Iron Oxide Nanoparticles Part (a): Preparation of Diluted Aqueous Ferrofluid Stable in Acidic Medium.

Magnetite nanoparticles were produced following the method of Massart (*Preparation of aqueous magnetic liquids in alkaline and acidic media*. IEEE Transactions on Magnetics, 1981. MAG-17(2): p. 1247-1248). In a typical reaction, 2M FeCl$_3$.6H$_2$O in 1M HCl (80 ml) and 1M FeCl$_2$.4H$_2$O in 1M HCl (40 ml) were mixed in a 2 L beaker and the mixture diluted to 1.2 L with MQ-water. NH$_4$OH (28% (w/w), 250 ml) was then quickly added and the mixture vigorously stirred for 30 minutes. After adding the NH$_4$OH, the colour of the mixture immediately turned from orange to black. Magnetite was then oxidized in acidic medium to maghemite by heating at 90° C. in the presence of iron nitrate for about an hour. The color of the suspension changed from black to reddish brown. Maghemite particles are then magnetically decanted, washed with acetone and finally peptized in water yielding a stable dispersion (5 wt %). The pH of the dispersion was about 1.5-2.

Part (b): Preparation of a poly(acrylic acid)10-block-poly (acrylamide)$_{20}$ Macro-RAFT Agent Using 2-{[butylsulfanyl) carbonothioyl]-sulfanyl}propanoic acid.

A solution of 2-{[butylsulfanyl)carbonothioyl]-sulfanyl}propanoic acid (0.75 g, 3.1 mmol), 4,4'-azobis(4-cyanovaleric acid) (0.05 g, 0.17 mmol), acrylamide (4.48 g, 63 mmol) in dioxane (18 g) and water (9 g) was prepared in a 100 mL round bottom flask. This was stirred magnetically and sparged with nitrogen for 15 minutes. The flask was then heated at 80° C. for 2 hrs. At the end of this period, acrylic acid (2.27 g, 31 mmol) and 2-{[butylsulfanyl)carbonothioyl] sulfanyl}propanoic acid (0.75 g, 3.1 mmol) were added to the flask. The mixture was deoxygenated and heating was continued at 80° C. for a further 3 hours. The copolymer solution had 21.8% solids.

Part (c): Deactivation of the RAFT Functionality in the poly (acrylic acid)$_{10}$-block-poly(acrylamide)$_{20}$ Macro-RAFT Agent from Part (b) Using Benzoyl Peroxide.

A 5 g of 21.8 wt % solution of the MacroRAFT of the copolymer (1.09 g, 0.454 mM) from part (b) was taken in a 250 ml round bottom flask containing 50 g of water and 25 g dioxane in it. Benzoyl peroxide (2.20 g, 9.08 mM) was then added. The solution in round bottom flask was stirred magnetically and sparged with nitrogen for 15 minutes. The flask was then heated at 80° C. for about 16 hours. At the end of this period, the yellow colour of the solution disappeared. The solution was then concentrated by distilling dioxane and water on rotary evaporator under reduced pressure. 40 g of the water added to it and the solution filtered on Whatman filter paper to remove decomposed initiator from it. The filtrate was colourless had 3.6% solids. It was then adjusted to 0.7% solids, pH 5.

Part (d): Preparation of Sterically Stabilized Iron Oxide Nanoparticles from the Aqueous Ferrofluid of Part (a) and the Modified Macro-Raft Agent of Part (c).

Nanoparticle dispersion (5 wt %) prepared in the part (a) (40 g) was diluted with MQ water to 200 g to yield 1 wt % dispersion of the nanoparticles. The pH of this nanoparticle dispersion prepared was then raised to 5. Solution of the modified Macro-RAFFT copolymer from part (c) (100 g) was then added. Mixture was vigorously stirred for 2 hours at room temperature to yield a sterically stabilized dispersion of nanoparticles in water. The dispersion was then dialysed to remove salts and unbound polymer. Bigger particles in the dispersion were removed by ultracentrifugation. The purified nanoparticle dispersion was then distilled to increase the solids loading of the ferrofluid dispersion to about 55 wt %.

Part (e): Preparation of poly(isobutylene) Succinic Anhydride Diethylethanol Amine (PIBSADEEA) Solution in Dodecane.

PIBSADEEA (2.0 g) was dissolved in dodecane (48 g) in a 100 mL beaker to yield a 4% solution.

Part (f): Preparation of poly(acrylamide) Matrix Encapsulated Fe2O3 from the Water-Based Ferrofluid of Part (d) and PIBSADEEA Solution of Part (e).

Water based ferrofluid prepared in part (d) (1 g) was mixed with acrylamide (0.45 g, 6.3 mmol), N,N'-methylenebisacrylamide (0.045 g, 0.29 mmol) and 4,4'-azobis(4-cyanovaleric acid) (0.0315 g, 0.112 mmol) in a 10 ml scintillation vial. PIBSADEEA solution from part (e) (2 g) was then added to the scintillation vial and the mixture emulsified on a vortex mixer for about 1 minute. The emulsion thus obtained was then blended with the balance of the PIBSADEEA solution of part (e) in a 100 ml round bottom flask. The resulting inverse emulsion was stirred mechanically, sparged with nitrogen for 15 minutes and held in an oil bath at 80° C. for about 6 hours. Acetone was used to wash away the dodecane from the resulting microspheres, which were then dried. The dry microspheres had diameters in the range of about 10 to 40 microns, a $Fe_2O_3$ content of 715 mg/g. When the beads were dispersed in agar and exposed to an oscillating magnetic field of 100 kHz and 90 Oe, they generated heat at a rate of 7.5 W/g.

The reference in this specification to any prior publication (or information derived from it), or to any matter which is known, is not, and should not be taken as an acknowledgment or admission or any form of suggestion that that prior publication (or information derived from it) or known matter forms part of the common general knowledge in the field of endeavour to which this specification relates.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

The invention claimed is:

1. Polymer microgel beads having a polymeric matrix that can absorb and be swollen by an aqueous liquid, the polymeric matrix having nanomagnetic particles dispersed substantially uniformly therethrough in an amount of at least 20 wt % relative to the total mass of the beads, wherein a steric stabiliser is associated with the particles, the steric stabiliser being a polymeric material that (i) does not form part of the polymeric matrix of the beads, and (ii) comprises a steric stabilising polymeric segment and an anchoring polymeric segment, wherein the steric stabilising polymeric segment is different from the anchoring polymeric segment, and wherein the anchoring polymeric segment has an affinity toward the surface of the nanomagnetic particles and secures the stabiliser to the particles.

2. The polymer microgel beads according to claim 1, wherein the beads have a size ranging from about 10 microns to about 50 microns.

3. The polymer microgel beads according to claim 1, wherein nanomagnetic particles have a size of less than 50 nm.

4. The polymer microgel beads according to claim 1, wherein nanomagnetic particles are present in at amount of at least 30 wt. %.

5. The polymer microgel beads according to claim 1, wherein nanomagnetic particles are selected from iron, nickel, chromium, cobalt, oxides thereof and combinations thereof.

6. The polymer microgel beads according to claim 1, wherein nanomagnetic particles are selected from magnetite ($Fe_3O_4$), maghemite ($\gamma$-$Fe_2O_3$) and combinations thereof.

7. The polymer microgel beads according to claim 1, wherein the polymeric matrix of the beads comprises a polymerised residue of at least one monoethylenically unsaturated monomer selected from acrylic acid, methacrylic acid, hydroxyethyl methacrylate, hydroxypropyl methacrylate, acrylamide and methacrylamide, hydroxyethyl acrylate, N-methylacrylamide, dimethylaminoethyl methacrylate, itaconic acid, p-styrene carboxylic acids, p-styrene sulfonic acids, vinyl sulfonic acid, vinyl phosphonic acid, ethacrylic acid, alpha-chloroacrylic acid, crotonic acid, fumaric acid, citraconic acid, mesaconic acid, maleic acid, 2-(dimethyl amino) ethyl and propyl acrylates and methacrylates, and 3-(diethylamino)ethyl and propyl acrylates and methacrylates; and at least multiethylenically unsaturated monomer selected from ethylene glycol di(meth)acrylate, triethylene glycol di(meth)acrylate, tetraethylene glycol di(meth)acrylate, 1,3-butylene glycol di(meth)acrylate, trimethylolpropane tri(meth)acrylate, 1,4-butanediol di(meth)acrylate, neopentyl glycol di(meth)acrylate, 1,6-hexanediol di(meth) acrylate, pentaerythritol di(meth)acrylate, pentaerythritol tri (meth)acrylate, pentaerythritol tetra(meth)acrylate, glycerol di(meth)acrylate, glycerol allyloxy di(meth)acrylate, 1,1,1-tris(hydroxymethyl)ethane di(meth)acrylate, 1,1,1-tris(hydroxymethyl)ethane tri(meth)acrylate, 1,1,1-tris(hydroxymethyl)propane di(meth)acrylate, 1,1,1-tris(hydroxymethyl) propane tri(meth)acrylate, triallyl cyanurate, triallyl isocyanurate, triallyl trimellitate, diallyl phthalate, diallyl terephthalte, divinyl benzene, methylol(meth)acrylamide, triallylamine, oleyl maleate, glyceryl propoxy triacrylate, allyl methacrylate, and methylenebis(meth)acrylamide.

8. The polymer microgel beads according to claim 1, wherein the steric stabiliser has a number average molecular weight ranging from about 1,000 to about 3,000.

9. The polymer microgel beads according to claim 1, wherein at least one of the steric stabilising polymeric segment and the anchoring polymeric segment is derived from one or more ethylenically unsaturated monomers that have been polymerised by living polymerisation.

10. The polymer microgel beads according to claim 1, wherein the steric stabilising polymeric segment comprises polyacrylamide, polyethylene oxide, polyhydroxyethylacrylate, poly N-isopropylacrylamide, polydimethylamino-ethyl-methacrylate, polyvinyl pyrrolidone or a copolymer thereof.

11. The polymer microgel beads according to claim 1, wherein the anchoring polymeric segment comprises polyacrylic acid, polymethacrylic acid, polystyrene, polyitaconic acid, poly-p-styrene carboxylic acids, poly-p-styrene sulfonic acids, polyvinyl sulfonic acid, polyvinyl phosphonic acid, poly monoacryloxyethyl phosphate, poly-2-(methylacryloyloxy) ethyl phosphate, polyethacrylic acid, poly-alpha-chloroacrylic acid, polycrotonic acid, polyfumaric acid, polycitraconic acid, polymesaconic acid, polymaleic acid, poly-2-(dimethyl amino) ethyl and propyl acrylates and methacrylates, poly-3-(diethyl amino) ethyl and propyl acrylates and methacrylates, polydimethylaminoethyl-methacrylate, or a copolymer thereof.

12. The polymer microgel beads according to claim 1, wherein the anchoring polymeric segment comprises at least 5 polymerised monomer residues that each provide a site that functions to secure the stabiliser to the particles.

13. The polymer microgel beads according to claim 1 further comprising one or more radioactive isotopes.

14. A method of preparing polymer microgel beads incorporating nanomagnetic particles, the method comprising:
providing a dispersion comprising a continuous organic phase and a dispersed aqueous phase, the dispersed aqueous phase comprising:
(i) one or more ethylenically unsaturated monomers that are soluble in the aqueous phase; and
(ii) nanomagnetic particles dispersed throughout the aqueous phase, the particles being maintained in their dispersed state by a steric stabiliser, wherein the steric stabiliser is a polymeric material comprising a steric stabilising polymeric segment and an anchoring polymeric segment, wherein the steric stabilising polymeric segment is different from the anchoring polymeric segment, and wherein the anchoring polymeric segment has an affinity toward the surface of the particles and secures the stabiliser to the particles; and
polymerising the one or more ethylenically unsaturated monomers to thereby form the polymer microgel beads incorporating the nanomagnetic particles.

15. A composition suitable for administration to subject, the composition comprising a pharmacologically acceptable carrier and polymer microgel beads in accordance with claim 1.

16. A composition in accordance with claim 15 in the form of an aqueous or non-aqueous sterile injectable solution which optionally contains one or more of an anti-oxidant, buffer, bactericide or solute which renders the composition isotonic with the blood of the intended subject.

17. A method for heating a target site of interest in a subject, the method comprising:
(i) administering a composition according to claim 15 to the subject; and
(ii) exposing at least the target site of interest to a magnetic field of a clinically acceptable frequency and strength such that the microgel beads from the composition radiate heat at the target site.

18. A method of performing hyperthermia therapy on a target site of interest in a subject, the method comprising administering a composition according to claim 15 to the subject and exposing at least the target site to a magnetic field of clinically acceptable frequency and strength to promote the hyperthermia therapy.

19. The method according to claim 18, wherein the target site of interest is cancerous tissue.

20. The method according to claim 17, wherein after administering the composition to the subject and exposing at least the target site to the magnetic field, the polymer microgel beads at the target site exhibit a volumetric absorption rate (VAR) of at least 1 Watts/cm$^3$.

21. The process of using a composition according to claim 15 in a method of performing hyperthermia therapy.

* * * * *